(12) United States Patent
Hinestroza et al.

(10) Patent No.: US 10,495,624 B2
(45) Date of Patent: Dec. 3, 2019

(54) NANOWIRE FUNCTIONALIZED FIBERS AND FABRICS

(71) Applicants: Cornell University, Ithaca, NY (US); University of Notre Dame du Lac, Notre Dame, IN (US)

(72) Inventors: Juan P. Hinestroza, Ithaca, NY (US); Masaru Kuno, Notre Dame, IN (US); Maksym Zhukovskyi, Notre Dame, IN (US)

(73) Assignees: Cornell University, Ithaca, NY (US); University of Notre Dame du Lac, Notre Dame, IN (US)

( * ) Notice: Subject to any disclaimer, the term of this patent is extended or adjusted under 35 U.S.C. 154(b) by 411 days.

(21) Appl. No.: 15/007,473

(22) Filed: Jan. 27, 2016

(65) Prior Publication Data

US 2016/0216248 A1 Jul. 28, 2016

Related U.S. Application Data

(60) Provisional application No. 62/108,209, filed on Jan. 27, 2015.

(51) Int. Cl.

| | | |
|---|---|---|
| *G01N 33/36* | (2006.01) | |
| *G01J 1/42* | (2006.01) | |
| *G01J 3/42* | (2006.01) | |
| *G01J 3/44* | (2006.01) | |
| *D06M 11/00* | (2006.01) | |
| *D06M 11/83* | (2006.01) | |
| *D06M 23/08* | (2006.01) | |
| *D21H 21/48* | (2006.01) | |
| *B82Y 30/00* | (2011.01) | |
| *D06M 11/44* | (2006.01) | |
| *D06M 11/46* | (2006.01) | |
| *D06M 11/53* | (2006.01) | |
| *D06M 11/58* | (2006.01) | |

(Continued)

(52) U.S. Cl.
CPC ............. *G01N 33/36* (2013.01); *D06M 11/00* (2013.01); *D06M 11/83* (2013.01); *D06M 23/08* (2013.01); *D21H 21/48* (2013.01); *G01J 1/42* (2013.01); *G01J 3/42* (2013.01); *G01J 3/44* (2013.01); *A41D 31/00* (2013.01); *B82Y 30/00* (2013.01); *D06M 11/44* (2013.01); *D06M 11/46* (2013.01); *D06M 11/53* (2013.01); *D06M 11/58* (2013.01); *D06M 11/68* (2013.01); *D06M 2101/06* (2013.01); *D06M 2101/28* (2013.01); *D06M 2101/34* (2013.01)

(58) Field of Classification Search
CPC .. G01N 33/36; D01F 8/02; D01F 8/08; D01F 8/12; G01J 3/42; G01J 3/44
USPC ............................................. 250/216, 227.11
See application file for complete search history.

(56) References Cited

U.S. PATENT DOCUMENTS

2010/0260998 A1* 10/2010 Waicukauski ......... B82Y 30/00
428/300.1

* cited by examiner

*Primary Examiner* — Kevin K Pyo
(74) *Attorney, Agent, or Firm* — Hodgson Russ LLP

(57) ABSTRACT

Provided are nanowire-coated fibers and compositions comprising one or more nanowire-coated fibers and methods of making the fibers and compositions. The fibers can be organic or inorganic fibers. The nanowires can be metallic or semiconducting nanowires. The nanowires are disposed on at least a portion of a surface of a fiber or fibers. The fibers and compositions can be used as barcodes (e.g., for anti-counterfeiting methods). The fibers and compositions also can be used as photodetectors (e.g., methods of detecting electromagnetic radiation).

22 Claims, 28 Drawing Sheets

(51) Int. Cl.
*D06M 11/68* (2006.01)
*D06M 101/06* (2006.01)
*D06M 101/28* (2006.01)
*D06M 101/34* (2006.01)
*A41D 31/00* (2019.01)

NANOWIRE FUNCTIONALIZED FIBERS AND FABRICS

CROSS-REFERENCE TO RELATED APPLICATIONS

This application claims priority to U.S. provisional patent application No. 62/108,209, filed Jan. 27, 2015, the disclosure of which is incorporated herein by reference.

FIELD THE DISCLOSURE

The present disclosure generally relates to nanowire-functionalized fibers. More particularly, the present disclosure relates to organic or inorganic fibers functionalized with metallic or dielectric nanowires.

BACKGROUND OF THE DISCLOSURE

Cotton—a natural fiber consisting of 90% cellulose—has been widely used for centuries. To expand its properties and use, numerous studies have since explored functionalizing cotton with different metal, semiconductor, organic, and carbon-based materials. Resulting hybrid cotton textiles exhibit enhanced properties and incorporate the unique mechanical, optical, and electrical properties of these systems. As examples, cotton/metal (Ag, Au, Cu, Pd, and Pt) composites possess conductive and/or catalytic properties useful in medical, photocatalytic, and electronic applications. Wide gap semiconductor functionalized cotton (e.g., with $TiO_2$ or ZnO) shows good UV-blocking properties, exhibits self-cleaning behavior, and possesses antibacterial properties. Cotton textiles have been modified with carbon nanotubes to obtain features such as enhanced mechanical properties, flame retardation, and hydrophobicity.

SUMMARY OF THE DISCLOSURE

The present disclosure relates to, for example, the general functionalization of cotton and other cellulosic fiber or fabrics using solution-synthesized CdSe and CdTe nanowires (NWs). In various examples, conformal coatings onto individual cotton fibers have been achieved through various physical and chemical approaches. Examples involve the electrostatic attraction of NWs to cotton charged positively with a Van de Graaff generator or via 2,3-epoxypropyltrimethylammonium chloride treatments. Resulting NW-functionalized textiles can consist of dense, conformal coatings and have been characterized for their UV-visible absorption, structure based on electron microscopy, and Raman activity.

In a first embodiment, an organic or inorganic fiber has one or more nanowires having a cross-sectional diameter of 1 to 75 nm and a length of 1 to 10 microns disposed on at least a portion of a surface of the fiber. The fiber can be an organic fiber such as a cellulose fiber, polyacrylonitrile (PAN) fiber, or a polyamide fiber. The fiber also can be an inorganic fiber such as a zirconia fiber. The nanowires can be comprised of CdSe, CdTe, CdS, ZnO, ZnS, ZnSe, ZnTe, PbS, PbSe, PbTe, $PbSe_xS_{1-x}$, wherein x is 0 to 1, InN, InP, InAs, GaP, GaN, GaAs, $TiO_2$, or combinations thereof. The nanowire can be bound to the fiber via electrostatic forces, van der Waal forces, covalent bonds, or a combination thereof. The fiber also can have one or more metal nanoparticles disposed on at least a portion of a fiber surface and/or at least a portion of a nanowire surface.

In a second embodiment, a composition comprises a plurality of the fibers of the first embodiment. The composition can be a plurality of woven fibers.

In a third embodiment, a method of making the fiber of the first embodiment or the composition of the second embodiment is provided. The method comprises: a) contacting a precursor fiber or plurality of precursor fibers with a suspension comprising nanowires in a solvent; b) removing the precursor fiber or precursor fibers from the suspension, wherein one or more nanowires are disposed on at least a portion of a surface of the precursor fiber or precursor fibers; and c) drying the fiber or fibers from b) to provide the fiber of the first embodiment or the composition of the second embodiment. The precursor fiber can comprise cationic cellulose, anionic cellulose, ester-modified cellulose, or mercized cotton.

The method can further comprise irradiating the suspension with broadband visible light while the precursor fiber or precursor fibers is/are dipped into the suspension. The broadband visible light can have a power density of at least 100 mW/cm2 and/or a wavelength of 300 to 2000 nm.

The method can further comprise electrostatically charging the precursor fiber or precursor fibers to form a charged fiber prior to the dipping.

In a fourth embodiment, a method for determining the presence or absence of the fiber of the first embodiment or the composition of the second embodiment in a sample is provided. The method comprises: a) obtaining a test infrared, Raman, and/or x-ray fluorescence spectrum of the sample; b) comparing the test infrared, Raman, and/or x-ray fluorescence spectrum to at least one control infrared, Raman, and/or x-ray fluorescence spectrum, wherein the control infrared, Raman, and/or x-ray fluorescence spectrum is an infrared, Raman, or x-ray fluorescence spectrum of a control fiber or a control composition; and c) determining a presence of selected features of the control infrared, Raman, and/or x-ray fluorescence spectra in the test infrared, Raman, and/or x-ray fluorescence spectrum. The presence of the selected features of the control infrared, Raman, and/or x-ray fluorescence spectrum in the test infrared, Raman, and/or x-ray fluorescence spectrum is indicative of the presence of the fiber of the first embodiment or the composition of the second embodiment in the sample. A lack of the selected features of the control infrared, Raman, and/or x-ray fluorescence spectrum in the test infrared, Raman, and/or x-ray fluorescence spectrum is indicative of the absence of the fiber of the first embodiment or the composition of the second embodiment in the sample. The sample can be paper currency comprising cellulose.

In a fifth embodiment, a method for determining presence or absence of electromagnetic radiation having a wavelength of 300 to 3000 nm is provided. The method comprises: a) providing the fiber of the first embodiment or the composition of the second embodiment, wherein the fiber or fibers absorb electromagnetic radiation having a wavelength of 300 to 3000 nm; and b) determining magnitude of an electrical current. Generation of an electrical current is indicative of the presence of electromagnetic radiation having a wavelength of 300 to 3000 nm. Absence of the generation of an electrical current is indicative of absence of electromagnetic radiation having a wavelength of 300 to 3000 nm. The intensity of the electromagnetic radiation present can be based on a magnitude of the electrical current.

In a sixth embodiment, an article of manufacture is provided. The article of manufacture comprises the fiber of the first embodiment or the composition of the second embodiment. The article of manufacture can be an article of clothing, a tent, a portable shelter, truck covering, window covering, umbrella, wallet, handbag, briefcase, bookbag, piece of luggage, watch, or piece of jewelry. The article of clothing can be a shirt, a jacket, pants, hat, dress, sweater, shoe, scarf, glove, belt, or a coat.

DESCRIPTION OF THE DISCLOSURE

Figure 1:
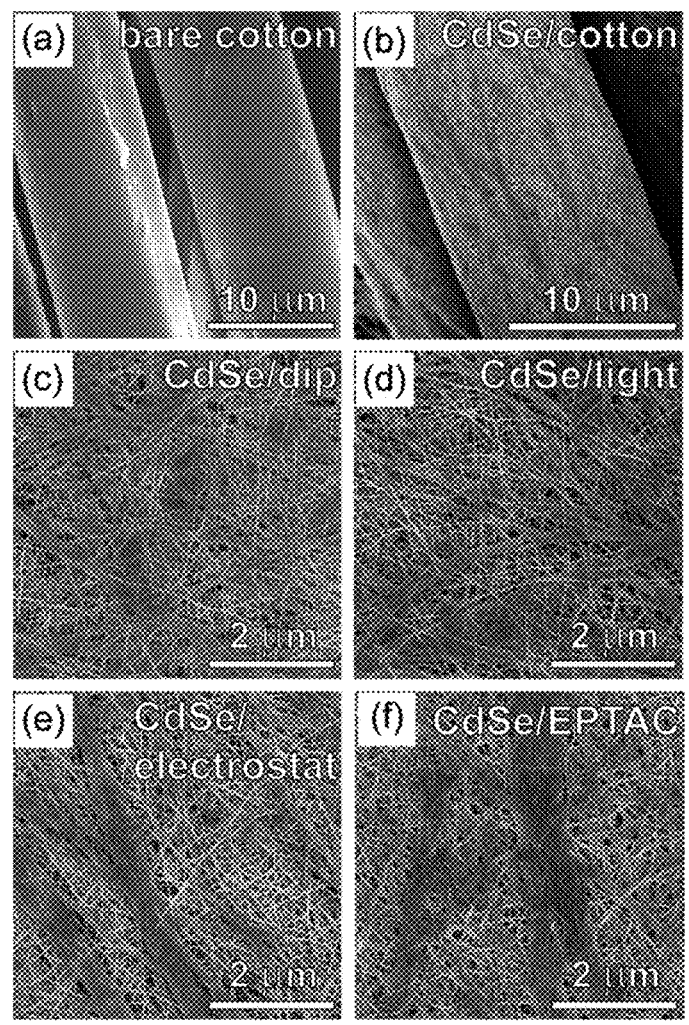
FIG. 1. Low-resolution SEM images of (a) locally purchased cotton, and (b) cotton functionalized with CdSe NWs. Corresponding high-resolution SEM images are shown for cotton/CdSe NWs after (c) simple dip-coating deposition, (d) light-induced dip-coating deposition, (e) VDGG stimulated dip-coating deposition, and (f) dip-coating deposition onto cationized cotton.

The present disclosure provides nanowire-functionalized fibers. Also, provided are methods of making and methods of using nanowire-functionalized fibers.

Nanowires ("NWs") offer several advantages over nanoparticles, including the multiplication in their functionality as well as providing increased mechanical strength. Nanowires can exhibit better electrical connectivity in an interconnected network. Rather than undergo hopping transport as in a network of nanoparticles deposited on cotton, carriers can undergo band transport across individual wires with a minimum of junctions. Nanowires also can exhibit substantial absorption and emission polarization sensitivities. Hence, polarization sensitive devices can be made using these materials, which is in contrast to nanoparticles which do not exhibit such polarization sensitivities. Thus, polarization sensitive photodetectors are possible.

For example, the general functionalization of cotton fabrics using solution-synthesized CdSe and CdTe nanowires was demonstrated. Conformal coatings onto individual cotton fibers was achieved through various physical and chemical approaches. Some examples involve the electrostatic attraction of NWs to cotton charged positively with a Van de Graaff generator or via 2,3-epoxypropyltrimethylammonium chloride treatments. Resulting NW-functionalized textiles can have dense, conformal coatings and have been characterized for their UV-visible absorption as well as Raman activity. Potential uses of functionalized textiles was demonstrated in two exemplary demonstrations. The first entails barcoding cotton using the unique Raman signature of the NWs. Also demonstrated was the surface-enhancement of their Raman signatures using co-deposited Au. A second demonstration takes advantage of the photoconductive nature of dielectric NWs to create cotton-based photodetectors. Apart from these illustrations, NW-functionalized cotton textiles may possess other uses in the realm of medical, anti-counterfeiting, and photocatalytic applications.

In an aspect, the present disclosure provides a nanowire-coating for fibers and fabrics that is robust and abrasion resistant. For example, the nanowire coating does not affect the properties of the textile. For example, the disclosure provides an organic or inorganic fiber having disposed on at least a portion of its surface one or more nanowires.

A fiber can be an organic fiber. Examples of suitable organic fibers include, but are not limited to, cellulose fibers, polyacrylonitrile (PAN) fibers, and polyamide fibers (e.g., nylon fibers).

A fiber can be an inorganic fiber. An example of an inorganic fiber is zirconia fibers.

A fiber or fibers can be of any size. Examples of suitable sizes include 50 nm to 1 mm, including all values to the nm and ranges therebetween. For example, cellulose fibers from 50 μm to 80 μm in diameter can be used.

A variety of nanowires can be used. Nanowires are inorganic (e.g., metallic or dielectric). Dielectric nanowires (e.g., semiconductor nanowires) can have unique size-dependent optical and electrical properties. Without intending to be bound by any particular theory, this stems from confinement effects that arise when their physical dimensions are smaller than the natural length scales of electrons and holes in these materials. The NWs can be passivated with surfactant molecules. This can make the NWs compatible with industrially relevant solution processing technologies. Examples of suitable nanowires include, but are not limited to, CdSe, CdTe, CdS, ZnO, ZnS, ZnSe, ZnTe, PbS, PbSe, PbTe, $PbSe_xS_{1-x}$, wherein x is 0 to 1, including all values to 0.01 and ranges therebetween, InN, InP, InAs, GaP, GaN, GaAs, $TiO_2$, or combinations thereof. The nanowires can be comprised of the aforementioned materials. The nanowires can be synthesized via solution or via other methods known in the art. In an example, a nanowire is not a carbon nanotube.

Nanowires can have a cross-sectional diameter of 1 to 75 nm, including all values to 0.1 nm and ranges therebetween. Nanowires can have a length of 1 to 10 microns, including all values to 0.1 micron and ranges therebetween. Nanowires can have an aspect ratio (nanowire length/nanowire diameter) of 100 to 10,000, including all values to the 0.1 and ranges therebetween. In an instance, solution synthesized nanowires have a diameter of 10 nm with a corresponding length of 10 μm.

Nanowires are disposed on at least a portion of a surface of a fiber or fibers. In various example, nanowires coat at least 10%, 20%, 30%, 40%, 50%, 60%, 70%, 80%, 90%, 95%, or 99% of the surface area of a fiber or individual fibers of a composition comprising a plurality of fibers. In an example, nanowires coat 100% of the surface area of a fiber or fibers. Nanowires (e.g., individual nanowires) are bound to the fiber via electrostatic forces, van der Waal forces, covalent bonds, or a combination thereof.

Nanowires can provide a conformal coating of a fiber or fibers. For example, the nanowires can be in a 1 micron thick layer on a fiber.

The density of nanowires on a fiber or individual fibers of a composition comprising a plurality of fibers can vary. For example, the density can be from $10^{-6}$ nanowires/micron$^2$ to $10^3$ nanowire/micron$^2$.

Nanowire-coated fibers can have metal nanoparticles disposed on at least a portion of a fiber surface and/or at least a portion of the nanowire surface. Examples of suitable nanoparticles include gold, nickel, platinum, silver, cobalt, iron, aluminum nanoparticles. The metal nanoparticles can be a mixture of nanoparticles. In an example, the density of nanoparticles is less than or equal to approximately $1.8 \times 10^4$ nanoparticles/μm$^2$. In another example, the density of nanoparticles is from $1 \times 10^2$ nanoparticles/μm$^2$ to $1 \times 10^4$ nanoparticles/μm$^2$.

A nanowire-coated fiber or fibers can be present in a plurality of nanowire-coated fibers. A composition can comprise a fiber or plurality of fibers. For example, a nanowire-coated fiber is present in a plurality of woven fibers (e.g., a woven cloth or a fabric).

An article of manufacture can comprise a fiber or a composition comprising one or more fibers. For example, an article of clothing (e.g., a shirt, a jacket, pants, hat, dress, sweater, shoe(s), scarf, glove(s), belt, coat/outerwear), a textile (e.g., a cloth or yarn), a tent (e.g., a canvas tent), a portable shelter, truck covering (e.g., canvas coverings on a truck), drapes/curtains, umbrellas, wallet, handbags, briefcase, bookbag, piece of luggage, watch, piece of jewelry and the like can comprise a fiber or a composition comprising one or more fibers. It may be desirable to include a fiber or a composition comprising one or more fibers on an article of manufacture for tracking or anti-counterfeiting purposes.

A nanowire-coated fibers or nanowire-coated fibers can have desirable properties. For example, a fiber or fibers has a water absorbency of 1.5-3.0 g/g. For example, a fiber or fibers has a breaking load of 160-220 N. For example, a fiber or fibers has a ultimate tensile strength of 18-30 MPa. For example, a fiber or fibers has an ultimate tensile strain of 18-30%.

In an aspect, the present disclosure provides methods of making nanowire-functionalized fibers of the present disclosure. The methods are based on coating of fibers with preformed nanowires or nanowires formed in situ during coating of the fibers. Individual nanowire-functionalized fibers or compositions comprising nanowire-functionalized fibers can be made using a method described herein.

For example, a method for making a nanowire-coated fiber or a composition comprising one or more nanowire-coated fibers comprises: a) contacting (e.g., dipping) a precursor fiber or plurality of precursor fibers with a suspension comprising nanowires in a solvent, b) removing the precursor fiber or precursor fibers from the suspension, wherein one or more nanowires are disposed on at least a portion of a surface of the precursor fiber or precursor fibers; and c) optionally, drying the fiber or fibers from b) to provide a nanowire-coated fiber or a composition comprising one or more nanowire-coated fibers.

A variety of precursor fibers can be used. Examples of suitable precursor fibers include, but are not limited to, cationic cellulose, anionic cellulose, ester-modified cellulose, or mercized cotton. A precursor fiber or fibers can comprise one of the aforementioned materials. The fibers described herein can be precursor fibers.

It is desirable that the precursor fiber be charged. Accordingly, the suspension comprising nanowires in a solvent can be irradiated with broadband visible light (it is desirable that the light have a wavelength in the absorption band of the nanowires) while the precursor fiber or precursor fibers is/are contacted with (e.g., dipped into) the suspension. Without intending to be bound by any particular theory, it is considered that irradiation with broadband visible light, in particular light having a wavelength in the absorption band of the nanowires, while the precursor fiber or precursor fibers is/are contacted with (e.g., dipped into) the suspension causes optical transitions in the nanowires (e.g., metallic and/or dielectric nanowires). This creates electrons and holes (the absence of an electron in the material's valence band which basically acts as a positively charge pseudoparticle analogous to the electron). These charges then undergo a variety of recombination processes including the emission of light. However, a fraction of them are trapped by surface defects, which prevents their recombination and results in charged nanowires. For example, the broadband visible light has a power density of at least 100 mW/cm$^2$ and/or a wavelength of 300 to 2000 nm, including all nm values to the 0.1 and ranges therebetween. Broadband visible light can be provided by ambient light (e.g., sunlight or room lights) or external sources (e.g., lamps and lasers).

A fiber or fibers or precursor fiber or precursor fibers can also be charged triboelectrically. For example, a fiber or fibers or precursor fiber or precursor fibers are charged using a Van de Graaff Generator or physical methods (e.g., rubbing the fibers together such that the friction results in charged fibers) to form a charged fiber prior to the dipping.

A fiber or fibers or precursor fiber or precursor fibers can also be a charged fiber or charged fibers or charged precursor fiber or charged precursor fibers. For example, a fiber or fibers or precursor fiber or precursor fibers can be chemically functionalized to provide a charged fiber or charged fibers or charged precursor fiber or charged precursor fibers. Suitable chemical functionalization methods are known in the art. For example, a fiber or fibers or precursor fiber or precursor fibers can be chemically functionalized by chemical treatments such as, for example, EPTA treatment. For example, a fiber (e.g., cellulose or other cotton-fiber-containing material) can be cationized.

A precursor fiber or precursor fibers can be contacted with a nanowire suspension in a solvent in a variety of manners. For example, the contacting can be dipping or spray coating.

A nanowire-coated fiber or nanowire coated fibers can be dried using various processes. For example, a nanowire-coated fiber or nanowire coated fibers can be dried be exposing the fiber(s) to ambient conditions until they are dry. A nanowire-coated fiber or nanowire coated fibers also can be dried via irradiation with, for example, infrared light or by passing dry air over the nanowire-coated fiber or nanowire coated fibers.

In an aspect, the present disclosure provides methods of using nanowire functionalized fibers or compositions comprising one or more nanowire-functionalized fibers. The fibers and/or compositions can be used in a variety of manners. For example, nanowire-functionalized textiles can be used in various medical, anti-counterfeiting, and photocatalytic applications.

Nanowire functionalized fibers or compositions comprising one or more fibers can be used to provide a barcode on, for example, compositions comprising one or more nanowire-functionalized fibers (e.g., textiles comprising one or more nanowire functionalized fibers). For example, nanowire functionalized fibers or compositions comprising one or more fibers can be used in anti-counterfeiting methods. The spectral signature of the nanowire(s) on the fiber or fibers (e.g., unique Raman spectrum of fiber(s)) provides a barcode that can be used to identify a sample (e.g., an article of manufacture). Use of nanowire functionalized fibers or compositions comprising one or more fibers coated with metal nanoparticles can provide surface-enhancement of their Raman signatures and greater sensitivity of the barcode.

For example, a method for determining the presence or absence of a nanowire functionalized fiber or compositions comprising one or more nanowire functionalized fiber in a sample (e.g., an article of manufacture comprising one or more nanowire-functionalized fiber) comprising: a) obtaining a test infrared, Raman, and/or x-ray fluorescence spectrum of the sample; and b) comparing the test infrared, Raman, and/or x-ray fluorescence spectrum to one or more control infrared, Raman, and/or x-ray fluorescence spectrum, where the control infrared, Raman, and/or x-ray fluorescence spectrum is an infrared, Raman, or x-ray fluorescence spectrum of a control fiber or composition comprising a control fiber or control fibers. A presence of selected features of the one or more control infrared, Raman, and/or x-ray fluorescence spectrum in the test infrared, Raman, and/or x-ray fluorescence spectrum can be determined using, for example, direct, optical, or computerized inspection. The control fiber can have similar properties and/or composition as the sample. The presence of selected features of one or more of the control spectrum/spectra in the test spectrum/ spectra is indicative of the presence of the fiber or fibers in the sample. The lack of selected features (e.g., sufficient features to identify a particular fiber composition) of the control spectrum/spectra in the test spectrum/spectra is indicative of the absence of the fiber or fibers in the sample. The sample can be an article of manufacture described herein. The sample can be, for example, paper currency comprising cellulose or a portion thereof.

Nanowire-functionalized fibers or compositions comprising one or more nanowire-functionalized fibers can be used as photodetectors. For example, a method for determining the presence or absence of electromagnetic radiation having a wavelength of 300 to 3000 nm comprises: a) providing a nanowire-functionalized fiber or a composition comprising one or more nanowire-functionalized fiber, where the nanowire-functionalized fiber(s) can absorb or are configured to absorb electromagnetic radiation having a wavelength of 300 to 3000 nm, where the generation of an electrical current is indicative of the presence of electromagnetic radiation having a wavelength of 300 to 3000 nm and absence of the generation of an electrical current is indicative of the absence of electromagnetic radiation having a wavelength of 300 to 3000 nm Magnitude of an electrical current can be determined using, for example, direct or computerized inspection. The magnitude of the generated electrical current can be indicative of the intensity of the electromagnetic radiation present.

The steps of the methods described disclosed herein (e.g., in the examples) are sufficient to produce the fibers of the present disclosure or carry out the methods of use of the present disclosure. Thus, in an example, a method consists essentially of a combination of the steps of the methods disclosed herein. In another example, the method consists of such steps.

The following examples are presented to illustrate the present disclosure. They are not intended to be limiting in any manner.

Example 1

The following provides examples of nanowire-functionalized fibers of the present disclosure, methods of making the functionalized fibers, and methods of using the fibers.

In this example, it is shown that cotton can be functionalized with CdSe and CdTe NWs. The technique is general, and can be applied to other NW systems. Various approaches have been used to deposit CdSe and CdTe nanowires onto cotton, taking advantage of the ability to induce large dipoles in them using electric fields. Complementary chemical approaches exploit the ability to chemically cationize cotton fibers. Resulting NW-functionalized cotton fabrics exhibit similar mechanical properties as their nonfunctionalized counterparts. Furthermore, they are optically active, and exhibit sizable photoconductivities. Potential uses for these NW-functionalized textiles are demonstrated through two proof-of-concept applications. The first illustrates the barcoding of cotton using the unique Raman signature of the NWs. The second illustrates how NW photoconductivity can be exploited to make cotton-based photodetectors.

Materials.

Cotton fabrics were obtained from a local store. Additional standardized TIC-400 woven cotton fabrics were acquired from Textile Innovators, Inc. (Windsor, N.C.). 3-chloro-2-hydroxypropyl-trimethylammonium chloride (65% in water) (CHPTAC) was purchased from TCI America. Trioctylphosphine (TOP, 90.0%), pyridine (99.0%), octadecene (ODE, 90.0%), oleic acid (90.0%), cadmium oxide (99.9%+, metal basis), tellurium powder (99.8%), and NaOH crystals were purchased from Sigma Aldrich. Tri-n-octylphosphine oxide (TOPO, 99.0%) was purchased from Strem Chemicals. Bismuth(III) chloride (98.0%), and selenium powder (99.5%) were obtained from Acros. Stearic acid (98.0%) was acquired from Alfa Aesar. Decylphosphonic acid (98.0%) was purchased from PCI synthesis. Acetic acid (99.7%), acetone (99.9%), methanol (99.8%) and toluene (99.5%) were obtained from Fisher Scientific and VWR. All chemicals were used without further purification.

$BiCl_3$ Solution.

To initiate NW growth, a Bi catalyst solution is required. A 2 mM $BiCl_3$ solution was therefore prepared by dissolving $BiCl_3$ (12.6 mg, 40 µmol) in 20 mL of acetone.

TOPSe, TOPTe, and TOPS Solutions.

Chalcogen sources are required for NW growth. One molar trioctylphosphine selenide (TOPSe) was therefore prepared by mixing selenium powder (0.8 g, 10.0 mmol) and TOP (10.0 mL, 20.2 mmol) under nitrogen. The mixture was then stirred overnight and was stored in a glovebox. One-half molar trioctylphosphine telluride (TOPTe) was likewise prepared by mixing tellurium powder (0.6 g, 5.0 mmol) and TOP (10.0 mL, 20.2 mmol) in a three neck flask connected to a Schlenk line. The mixture was kept under vacuum at 100° C. for 1 h (h=hour or hours) to dry and degas the solvent. Afterward, the flask was backfilled with $N_2$ and was heated to 170° C. When the tellurium powder completely dissolved, the solution was cooled to room temperature and was subsequently stored in a glovebox. One molar trioctylphosphine sulfide (TOPS) was prepared by mixing sulfur powder (0.32 g, 10.0 mmol) and TOP (10.0 mL, 20.2 mmol) under nitrogen. The mixture was then stirred overnight and was stored in a glovebox.

Nanowire Synthesis.

Figure 8:
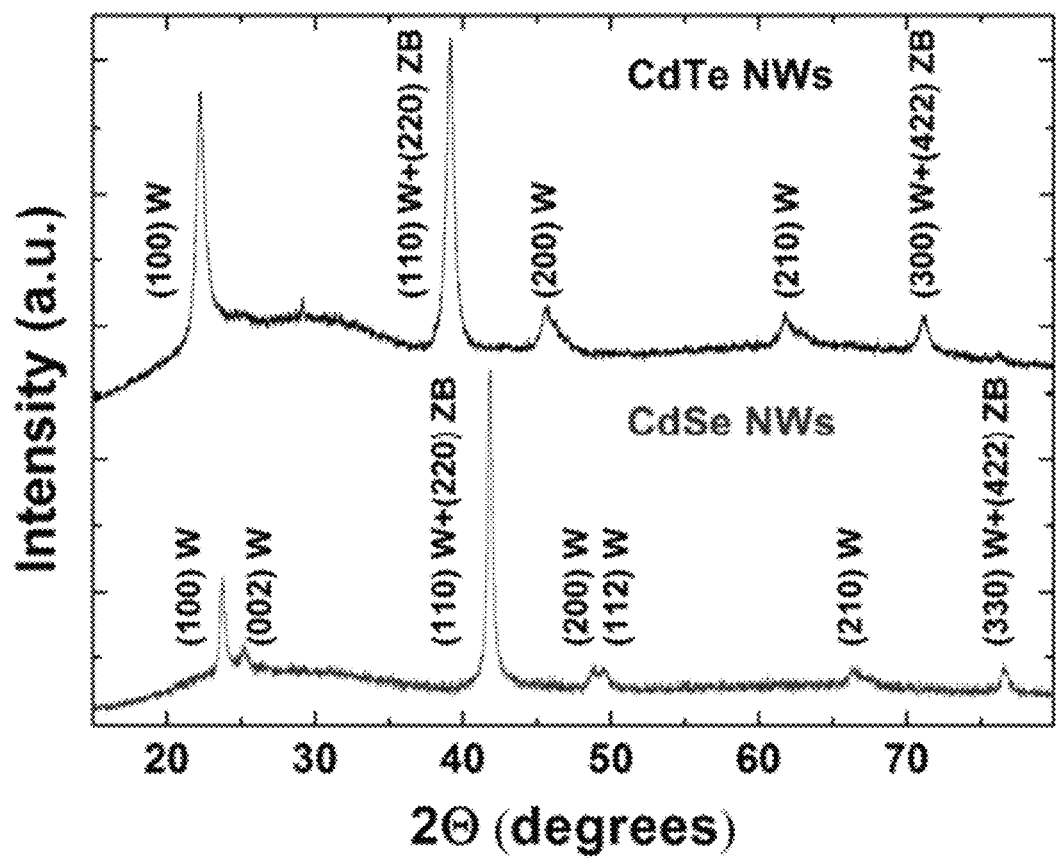
FIG. 8. XRD powder patterns for CdSe and CdTe NWs.

CdSe, CdTe and CdS NWs were synthesized using SLS growth. All NW samples were imaged with a transmission electron microscope (TEM, JEOL). Average diameters and lengths were determined using TEM vendor-provided software (sample size=100). Corresponding XRD powder patterns of CdSe and CdTe NWs can be found in the FIG. 8. Brief descriptions of NW syntheses follow.

CdSe NWs.

CdSe NWs were prepared following previously described methods with some modifications. To make CdSe NWs, TOPO (2.5 g, 6.5 mmol), cadmium oxide (25.0 mg, 0.2 mmol), and stearic acid (0.2 g, 0.7 mmol) were combined in a three-neck flask connected to a Schlenk line. The mixture was stirred under a vacuum at 150° C. for 1 h to dry and degas it. The reaction vessel was backfilled with $N_2$ and was heated to 350° C. When the initial red slurry turned clear, the temperature was lowered to 250° C. An injection solution, consisting of 1 M TOPSe (50.0 µL, 50.0 µmol) and 2 mM $BiCl_3$ in acetone (100.0 µL, 0.2 µmol), was then rapidly introduced into the three-neck flask. A dark-brown solution resulted due to the formation of NWs. The solution was subsequently left at 250° C. for two additional minutes and was cooled to 75° C. to stop the reaction. Toluene (15.0 mL) was added to prevent TOPO from solidifying. Produced NWs were precipitated from suspension by adding an excess of methanol (10.0 mL). The wires were recovered by centrifuging this mixture and were subsequently subjected to several toluene/methanol washing steps to remove any excess TOPO. Resulting NWs were stored in toluene.

CdTe NWs.

CdTe NWs were prepared following described methods with some modifications. TOPO (2.5 g, 6.5 mmol), CdO (25.0 mg, 0.2 mmol) and decylphosphonic acid (70.0 mg, 0.3 mmol) were combined in a three neck flask connected to a Schlenk line. The mixture was stirred under vacuum at 150° C. for 1 h in order to dry and degas it. The reaction vessel was backfilled with $N_2$ and was heated to 350° C. The initially red slurry became clear on prolonged heating. At this point, TOP (2.5 mL, 5.1 mmol) was added to the mixture and the temperature was decreased to 285° C. An injection solution consisting of 0.5 M TOPTe (50.0 µL, 25.0 µmol) and 2 mM $BiCl_3$ in acetone (50.0 µL, 0.1 µmol) was then introduced into the three-neck flask to initiate NW growth. The resulting solution turned dark-brown, indicating the presence of NWs. The mixture was left heating at 285° C. for two additional minutes and was cooled to 75° C. to stop the reaction. Toluene (15.0 mL) was added to prevent TOPO from solidifying whereupon the NWs were precipitated from the mixture by adding an excess of methanol (10.0 mL). The wires were recovered by centrifuging this suspension and were then subjected to several toluene/methanol washing steps to remove any excess surfactant. Obtained NWs were stored in toluene.

CdS NWs.

CdS NWs were prepared following the method described in ref 23 with some modifications. TOPO (1.0 g, 2.6 mmol), CdO (64.0 mg, 0.5 mmol), ODE (3 mL, 0.6 mmol) and oleic acid (0.4 mL, 1.3 mmol) were combined in a three neck flask connected to a Schlenk line. The mixture was stirred under vacuum at 150° C. for 1 h in order to dry and degas it. The reaction vessel was backfilled with $N_2$ and was heated to 315° C. When the initial red slurry turned clear, an injection solution, consisting of 1 M TOPS (50.0 µL, 50.0 µmol) and 2 mM $BiCl_3$ in acetone (50.0 µL, 0.1 µmol), was rapidly introduced into the three-neck flask to initiate NW growth. The resulting solution turned orange, indicating the presence of NWs. The mixture was left heating at 315° C. for two additional minutes and was cooled to 75° C. to stop the reaction. Toluene (15.0 mL) was added to prevent TOPO from solidifying whereupon the NWs were precipitated from the mixture by adding an excess of methanol (10.0 mL). The wires were recovered by centrifuging this suspension and were subjected to several toluene/methanol washing steps to remove any excess surfactant. Obtained NWs were stored in toluene.

Pyridine Treatment.

To improve nanowire transport properties in photoconductivity measurements, ligand exchange was performed to replace TOPO and other insulating surface species with pyridine. NWs were first isolated by centrifuging toluene suspensions. Pyridine (15.0 mL) was then added to the precipitate. The pyridine suspension was stirred at 65° C. for 30 min whereupon NWs were recovered by centrifuging the mixture. This washing procedure with pyridine was carried out three times, with the final precipitate stored in toluene.

Cationization of Cotton.

To improve the NW-to-cotton affinity, cotton samples were chemically modified through cationic functionalization. Briefly, under alkaline conditions, ammonium epoxides react with the OH groups of cellulose to create cotton with positively charged surfaces. A solution of 2,3-epoxypropyltrimethylammonium chloride (EPTAC) was therefore prepared by reacting 3-chloro-2-hydroxypropyl-trimethylammonium chloride (CHPTAC) with NaOH using a previously described procedure. The process consists of adding CHPTAC (33.3 g, 0.1 mol) and NaOH (15.2 g, 0.4 mol) to 66.7 mL of deionized water. Cotton fabrics (25×25 mm) were immersed into this solution and were recovered when thoroughly soaked. Samples were stored in plastic bags for 24 h at room temperature to complete the reaction. Specimens were subsequently rinsed with dilute acetic acid (17 mM) to neutralize the fabrics and were dried under ambient conditions. Mercerized cotton samples were obtained using an identical procedure but without the use of CHPTAC.

Cotton/NW Composites.

Figure 9:
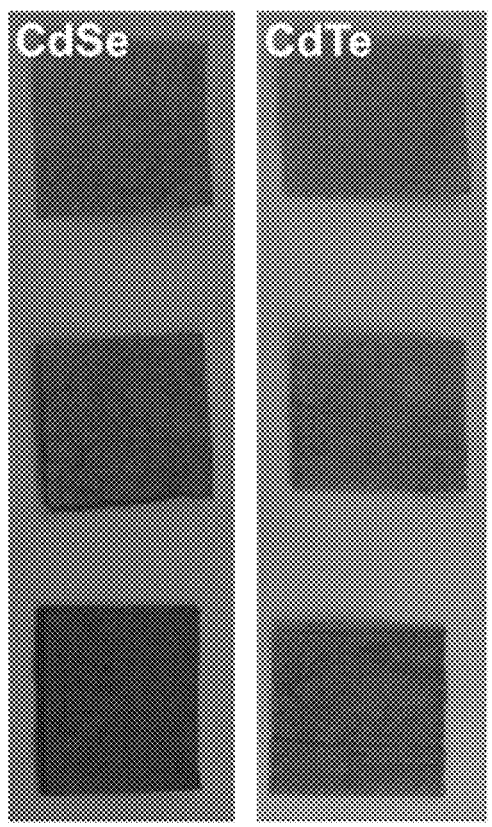
FIG. 9. Digital camera photos of cotton fabrics after dip-coating in CdSe and CdTe NWs solution. From top to bottom: cotton/NWs composites after simple dip-coating deposition; VDGG stimulated dip-coating deposition of NWs; and dip-coating deposition of CdSe NWs onto cationized cotton.
Figure 10:
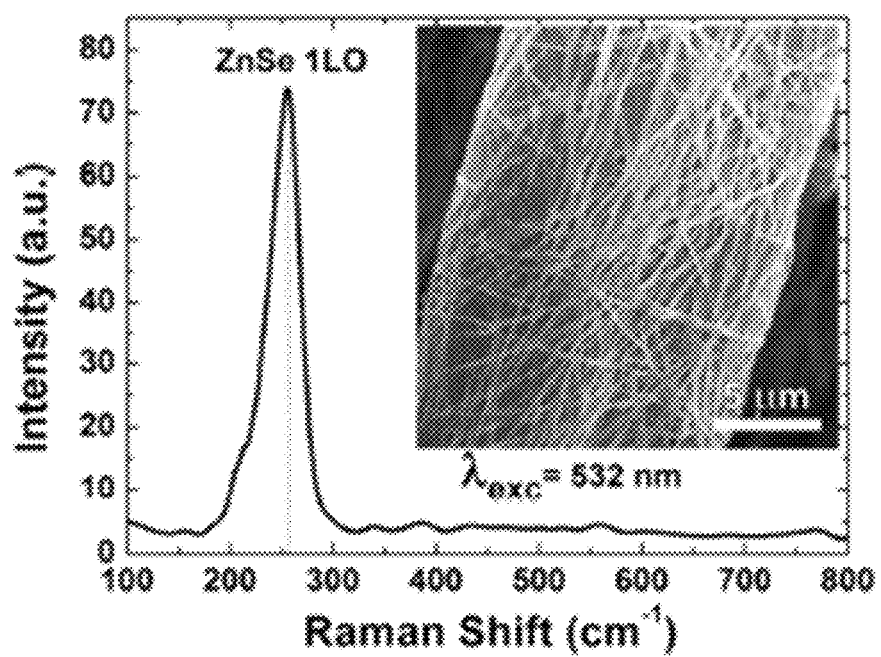
FIG. 10. Raman spectrum of cotton functionalized with ZnSe NWs (SEM image inset). The first longitudinal optical mode is visible at $\nu_{1LO}$=254 cm$^{-1}$.

NWs were deposited onto cotton textiles using several physical and chemical approaches. Physical approaches: (1) CdSe and CdTe NWs were adsorbed onto cotton by dipping cotton specimens into NW/toluene suspensions (NW concentration ~$3.7 \times 10^{-11}$ M); (2) by irradiating NW suspensions with broadband visible light (196.5 W/cm² at 630 nm) during dip-coating; (3) by electrostatically charging cotton fabrics prior to dip-coating using a 25 kV Van de Graaff generator (VDGG) (the resulting average surface voltage of the cotton was ~0.3 kV/cm² with a corresponding charge density of $5.8 \times 10^{-11}$ C/cm²). Chemical approaches: adsorbing CdSe and CdTe NWs onto (4) mercerized and (5) EPTAC-cationized cotton via dip-coating. For all approaches, dip-coating was carried out once. After dip-coating, cotton/NW samples were allowed to dry overnight under ambient conditions. Digital photographs of the as-produced fabrics can be found in FIG. 9. Cotton functionalization is not limited to CdSe and CdTe NWs but can also be applied using other 1D nanostructures (e.g., nanowires), such as ZnSe, ZnO, $TiO_2$, etc. To highlight this, ZnSe NWs were deposited onto cotton fabrics resulting in dense, conformal coatings. SEM images (see FIG. 10) and other details—including the ZnSe NW synthesis—are described herein.

Characterization.

Surface morphologies of bare cotton and NW-functionalized textiles were studied with a field-emission scanning electron microscope (SEM, FEI). Prior to observation, samples were sputter coated with 5 nm of iridium. Raman spectra were collected with a micro Raman spectrometer (Jasco) using 532 nm excitation. Absorption spectra were acquired in reflectance mode with a 60 mm integrating sphere on a Jasco spectrometer. Emission spectra were acquired using a microphotoluminescence setup based around an inverted optical microscope. A detailed description of this system was previously described. Photocurrent measurements were carried out by applying a bias voltage (+150 V) across Au electrodes (60 µm gap, associated electric field ~$2.5 \times 10^4$ V/cm; electrodes made by sputtering Au onto a microscope coverslip using a 60 µm copper wire as a shadow mask). Cotton/NW composites were then placed across the electrodes and were held in place with a second (nonpatterned) coverslip. The two coverslips were fastened together using epoxy. Tunable excitation from 450 to 850 nm was obtained from a supercontinuum white light source (Fianium) dispersed with an acousto-optic tunable filter. At a given excitation wavelength, the light was focused onto the sample using a visible achromatic doublet. The incident power on the sample was monitored with a variable wavelength power meter. Associated excitation intensities ranged from ~180 to ~430 mW/cm². A digital picoammeter (Kiethley) was used to measure resulting photocurrents.

Wettability.

Fabric samples were cut along the warp direction with dimensions of 10 mm (width)×25 mm (length). Wettability tests were conducted using a commercial tensiometer (KSV Sigma 700). Samples were lowered to the working liquid level with measurements carried out using distilled water as a wetting agent. The vertical wicking behavior of cotton/NW fabrics was determined by taking mass readings of water uptake as a function of time along the fabric's warp direction.

Mechanical Properties.

The tensile properties and break point elongation of cotton/NW fabrics were measured using a commercial tensile tester (Instron, model 5566). Fabric dimensions were 28×28 mm$^2$ The instrument gage length was set to 10±1 mm with a corresponding crosshead speed of 10 mm/min Breaking load, ultimate tensile strength, and ultimate tensile strain were measured along the fabric's warp direction.

Durability Test.

Figure 11:
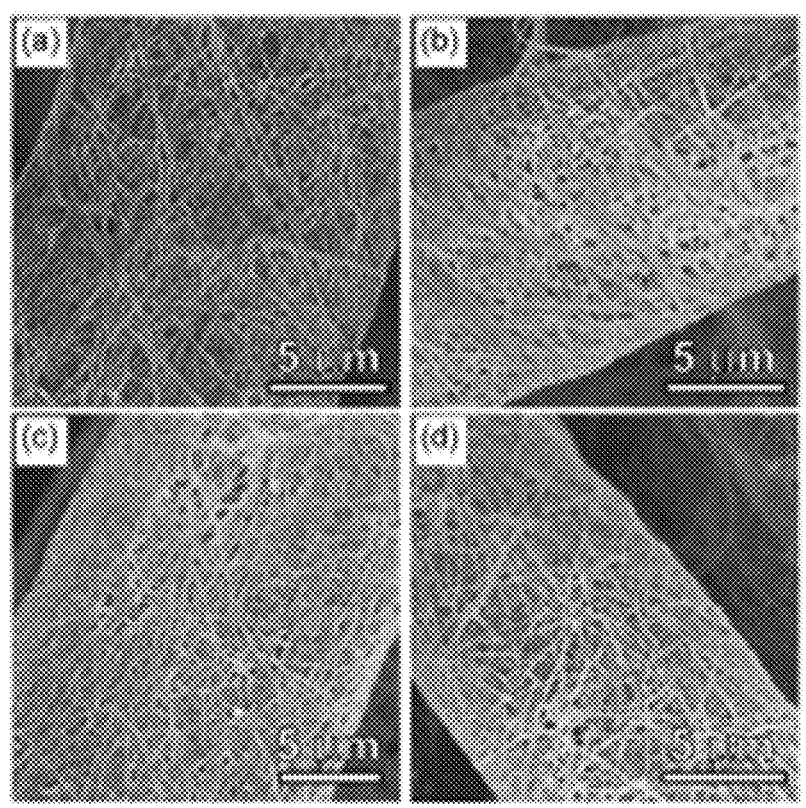
FIG. 11. SEM images of EPTAC-cotton/CdSe NW composites (a) before washing, (b) after 1 hour of continuous agitation in room temperature DI water, (c) after 1 hour of continuous agitation in 60° C. tap water/detergent solution (1 wt %), and (d) after 1 week of continuous agitation in 60° C. DI water. ICP-AES measurements show that only 0.025±0.004 ppm (mg/kg) of $Cd^{2+}$ was detected in the resulting DI water (one week washing period). As a point of reference, the EPA defines the maximum allowed concentration of cadmium in effluent waste to be 85 ppm. This is ~3400× higher than the amount of cadmium detected in the above experiment.

Durability tests were conducted on NW treated fabrics following a previously described procedure with some modifications. Three tests simulating normal garment washing procedures were conducted. In the first, sample swatches were soaked in room temperature DI water for one hour under continuous stirring. The second test involved soaking sample swatches in a 60° C. tap water/detergent solution (1 wt %) for 1 h under continuous stirring. For the third test, sample swatches were soaked in 60° C. DI water for one week under continuous stirring. After soaking, cotton fabrics were rinsed with tap water or DI water and were then dried in open air. Sample quality before and after the durability test was verified using SEM imaging. Additional details, including SEM images and inductively coupled plasma atomic emission spectroscopy (ICP-AES) measurements of the DI water after washing can be found in the FIG. 11.

Results and Discussion.

Figure 12:
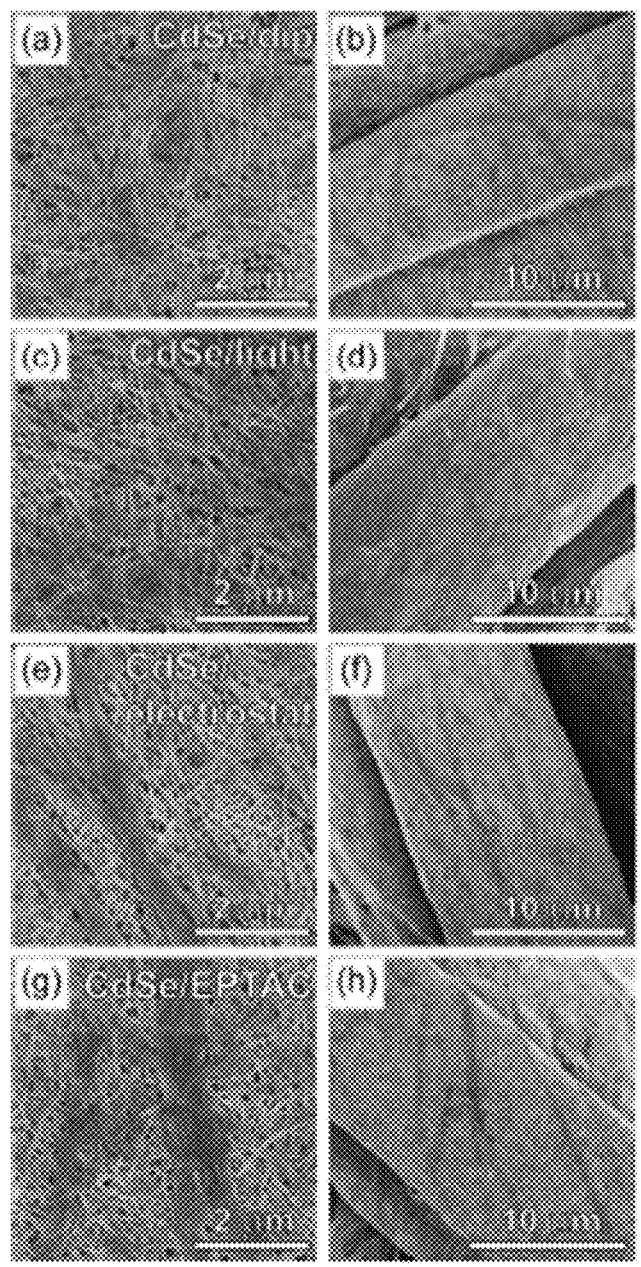
FIG. 12. High and low resolution SEM images of cotton/CdSe NW composites after (a-b) simple dip-coating, (c-d) light induced dip-coating, (e-f) VDGG stimulated dip-coating NW deposition and (g-h) dip-coating deposition onto cationized cotton.
Figure 13:
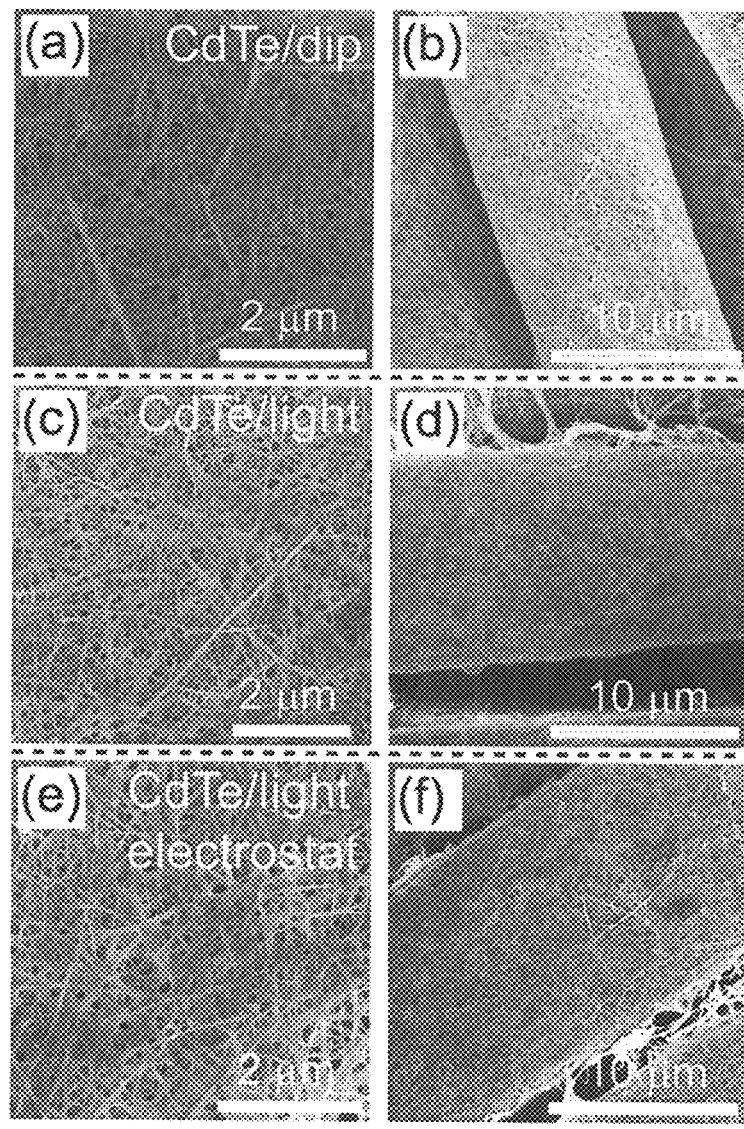
FIG. 13. SEM image of cotton/CdTe NW composites after (a-b) simple dip-coating, (c-d) light induced dip-coating, and (e-f) VDGG stimulated dip-coating NW deposition.
Figure 14:
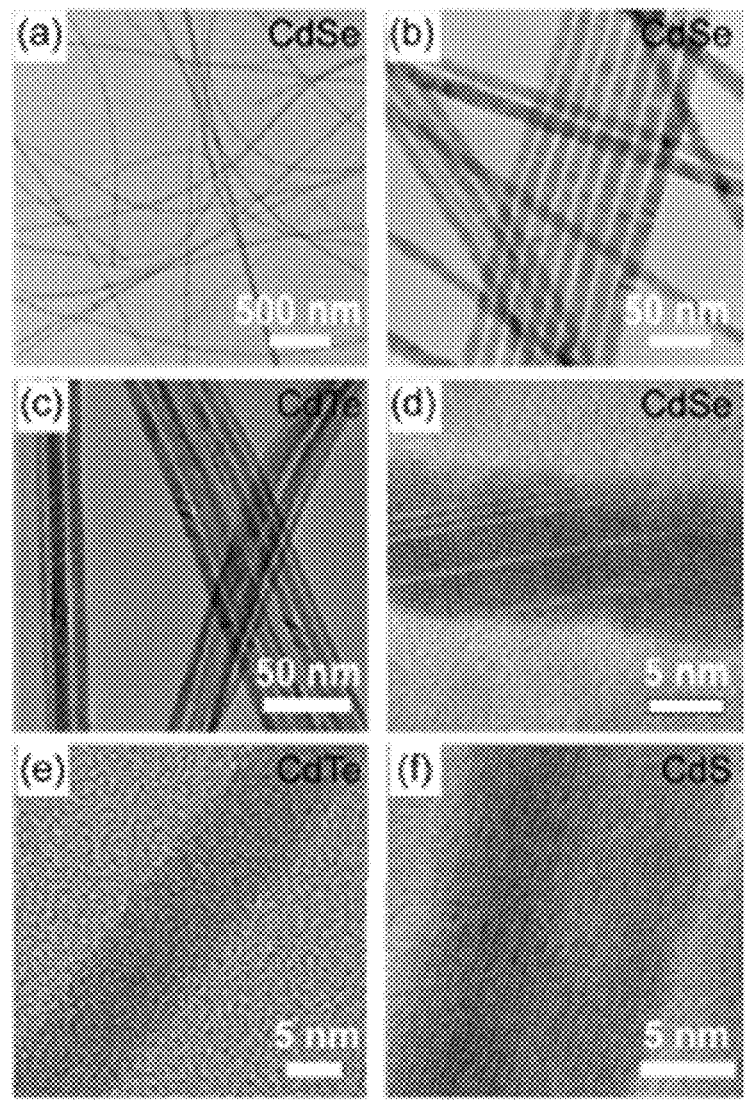
FIG. 14. TEM images of CdSe, CdTe, and CdS NWs. Low resolution TEM images of a)-b) CdSe, and c) CdTe NWs. High magnification TEM images of d) CdSe, e) CdTe, and f) CdS NWs. Average NW diameters are calculated using 100 different NWs.
Figure 15:
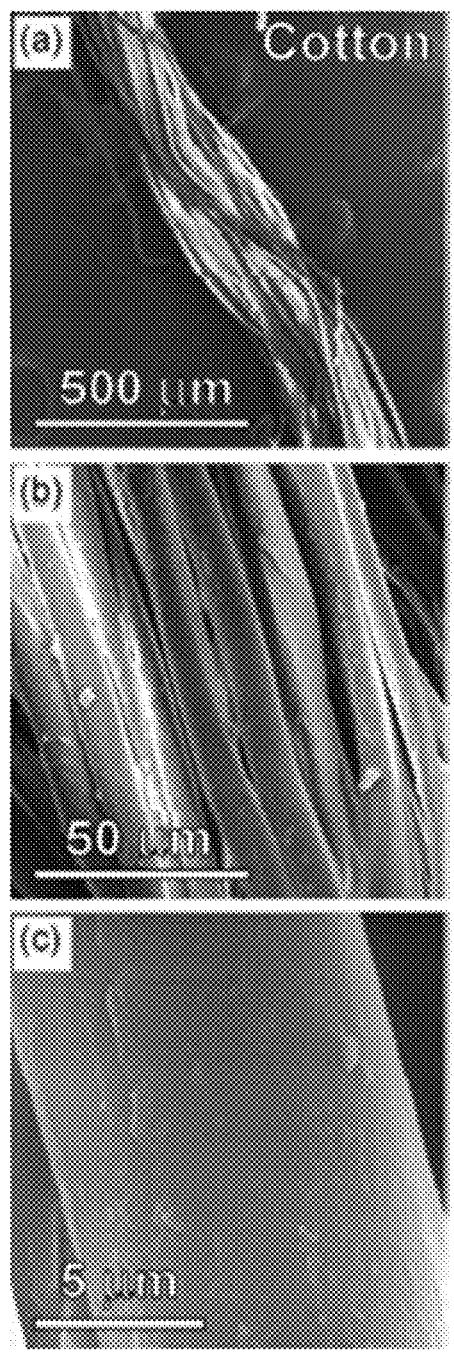
FIG. 15. SEM image of locally purchased cotton: (a-b) low magnification and (c) high magnification. Average size of the cotton fibers was estimated for 10 different fibers using SEM supported imaging software.

FIG. 1a shows an SEM image of unmodified locally purchased cotton fabric. Surfaces of individual cotton fibers are seen to be smooth. FIG. 1b-f shows complementary SEM images of fabrics functionalized with CdSe NWs (images of CdTe-functionalized cotton and additional images of CdSe functionalized are in FIGS. 12-13). In either case, individual cotton fibers exhibit dense, conformal coatings. This is due to the small dimensions of the NWs relative to those of individual cotton fibers. Specifically, average diameters of CdSe (CdTe) NWs are d=12.9±2.3 nm (d=9.9±1.8 nm) with lengths l=10-15 μm (see FIG. 14), whereas those of individual cotton fibers are d=10-12 μm with lengths up to 1 cm (see FIG. 15). FIG. 1 also reveals that the deposited NWs form an interlinked network that encapsulates individual cotton fibers. This characteristic could be important for applications involving abrasion and friction resistant cotton textiles. The NW's nanoscale dimensions also mean that cotton's intrinsic mechanical properties are retained.

Figure 16:
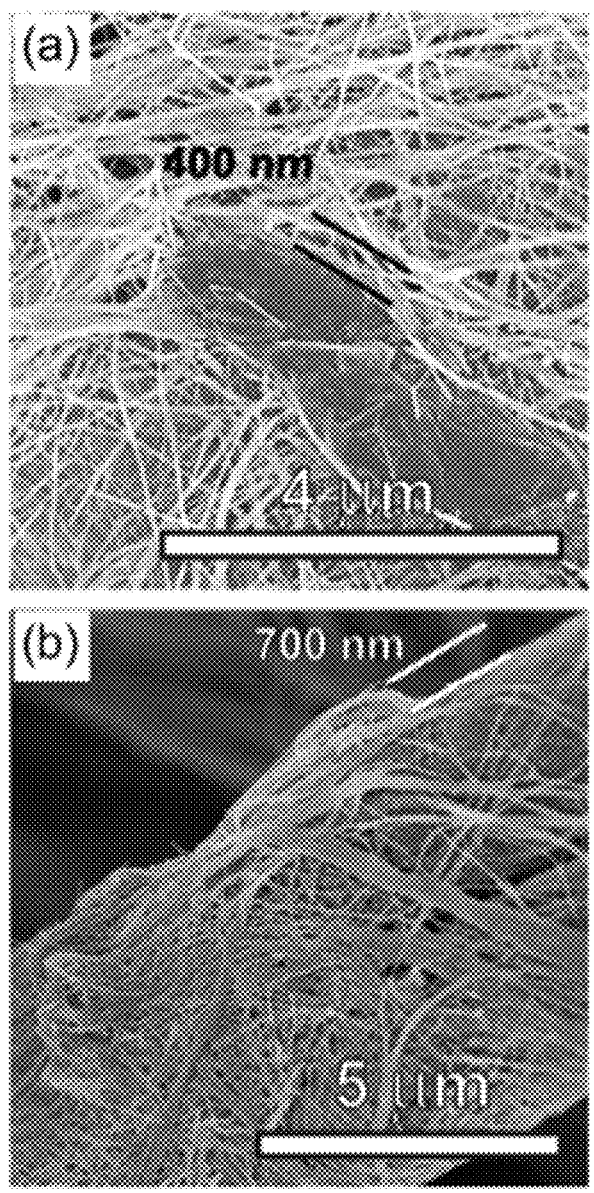
FIG. 16. Cross-sectional SEM images of cotton/CdSe NW composites. NW film thicknesses of ~400-700 nm are observed.

FIG. 1c-f show SEM images of cotton/CdSe NW composites made using different deposition approaches described herein. Either illuminating NW suspensions with light during dip-coating (FIG. 1d) or using a VDGG to charge the cotton (FIG. 1e) leads to the apparent formation of macroscopic NW bundles in solution. These bundles subsequently deposit onto cotton fibers. In the former case, this agglomeration may result from the light-induced dipole—dipole coupling of individual wires, which leads to an increased proclivity for NW bundling prior to deposition. This bundling phenomenon has previously been observed during the light-induced assembly of NW yarns. In the latter case where cotton has been charged with a VDGG prior to dip-coating, resulting electric fields may also enhance the likelihood of NW bundling through a similar mechanism. A tendency to form bundles is also observed when cotton is chemically cationized prior to dip-coating (FIG. 1f). Analogous results are found for cotton/CdTe NW textiles (see FIG. 13). In all cases, the NWs form a tight conformal network about individual cotton fibers, with a corresponding NW film thickness of ~400-700 nm (see FIG. 16).

Figure 17:
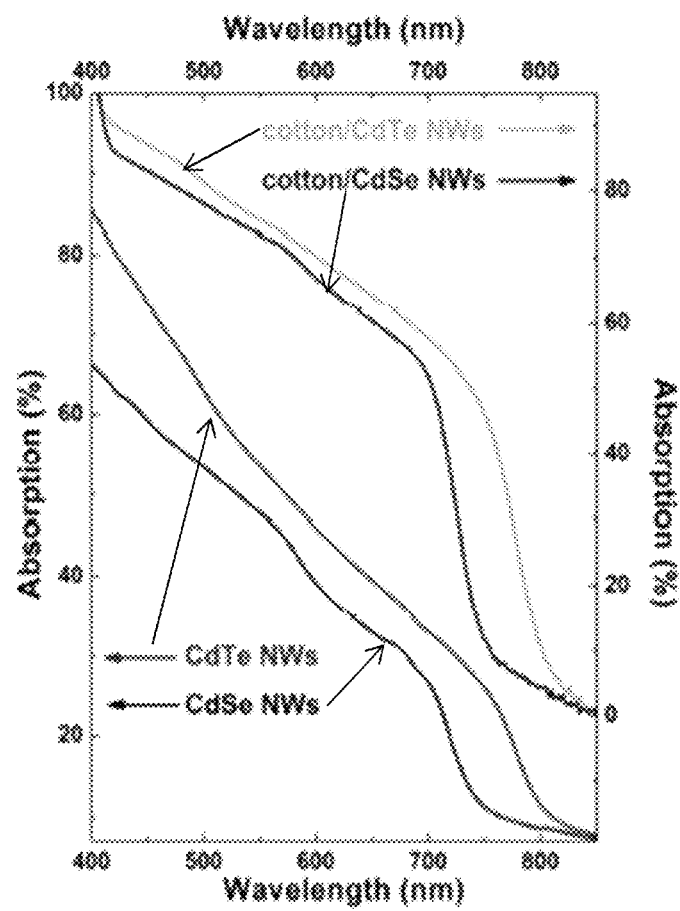
FIG. 17. Linear absorption spectra of CdSe and CdTe NW solutions and cotton/NW composites.

To assess the efficiencies of the various deposition approaches, absorption spectroscopy was conducted on functionalized cotton samples. Results are shown in FIG. 2a, where absorption spectra of cotton/CdSe NW composites are shown. Solution absorption spectra of CdSe (and CdTe) NWs are provided in FIG. 17 for comparison purposes. The cotton/CdSe NW fabrics exhibit an absorption onset at 720 nm in agreement with CdSe's bulk band gap of 1.74 eV (~712 nm). The absorption increases toward higher energies in a manner consistent with the increasing density of states of CdSe NWs. Furthermore, the data show that the amount of light absorbed by the functionalized fabrics increases when the dip-coating method (trace 1) is augmented with concurrent illumination of NW suspensions (trace 2), or by pretreating the dipped cotton with a VDGG (trace 3). Large absorption enhancements using both chemical functionalization approaches for cotton (traces 4 and 5) were observed. Of all the approaches investigated, EPTAC-cationized cotton textiles exhibit the largest absorbance values (trace 5). This indicates that NW deposition efficiencies increase as follows (from smallest to largest): dip-coating, light stimulated, VDGG stimulated, mercerized, and EPTAC functionalization.

Figure 18:
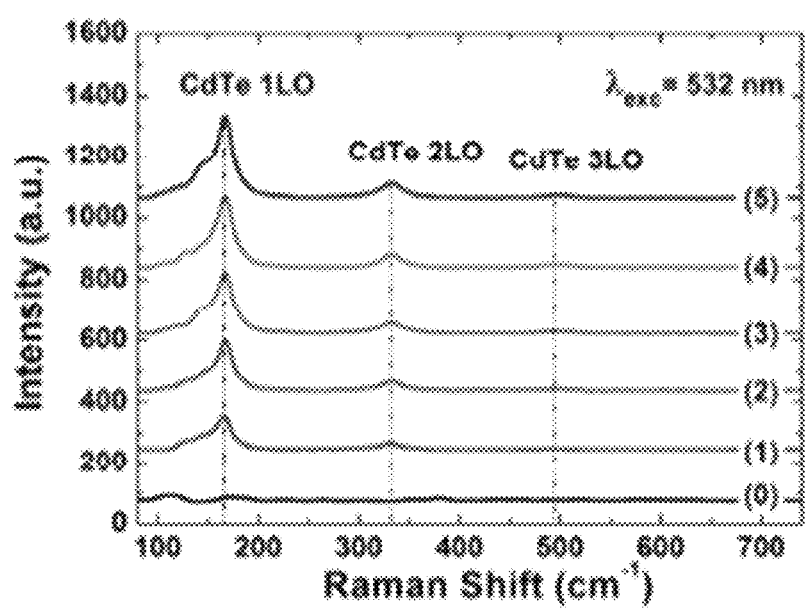
FIG. 18. Raman spectra of scientific grade (TIC 400) cotton/CdTe NW textiles made using different deposition approaches. CdTe's first and second longitudinal optical phonons are apparent [$\nu_{2LO}$=330 cm$^{-1}$, $\nu_{3LO}$=495 cm$^{-1}$], along with additional Raman peaks associated with the A1 and E modes of Te found on CdTe NW surfaces (possibly due to anodic corrosion). From bottom to top, the labeled traces are: (1) simple dip-coating deposition of NWs, (2) light-induced dip-coating of NWs, (3) VDGG stimulated dip-coating deposition of NWs, (4) dip-coating deposition of NWs onto mercerized cotton, and (5) dip-coating deposition of NWs onto cationized cotton. For comparison purposes, the Raman spectrum for bare cotton is shown as trace (0). Traces are offset for clarity.
Figure 19:
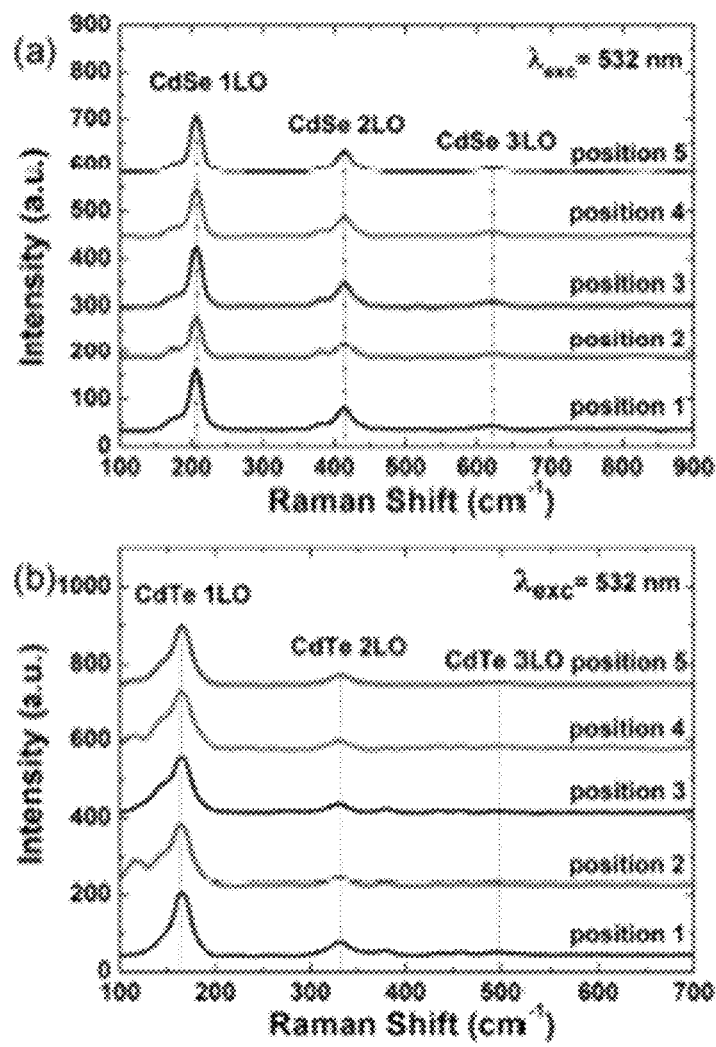
FIG. 19. Raman spectra of (a) locally purchased cotton/CdSe NW and (b) cotton/CdTe NW composites taken at 5 separate locations on textile.

To further establish the functionalization of cotton with CdSe and CdTe NWs, Raman spectra of cotton/NW composites were acquired. FIG. 2b shows Raman data taken on cotton/CdSe NW-functionalized textiles. For comparison purposes, the Raman spectrum of bare cotton is shown as trace 0. All cotton/CdSe NW Raman spectra show peaks related to the scattering of CdSe's longitudinal optical (LO) phonons. Specifically, the fundamental peak is observed at 205 cm$^{-1}$, along with its first (2LO) and second (3LO) overtones ($v_{2LO}$=410 cm$^{-1}$, $v_{3LO}$=615 cm$^{-1}$). Analogous results are found for CdTe NW-functionalized fabrics (see FIG. 18). On the basis of the intensities observed in FIG. 2b, these Raman spectra reveal the same trend in NW deposition efficiencies seen earlier in FIG. 2a. Namely, deposition efficiencies increase as: dip-coating, light stimulated, VDGG stimulated, mercerized, and EPTAC functionalization (see FIG. 18). The reproducibility of these Raman results has been confirmed by recording Raman spectra from different locations along functionalized cotton fibers. (See FIG. 19).

Figure 3:
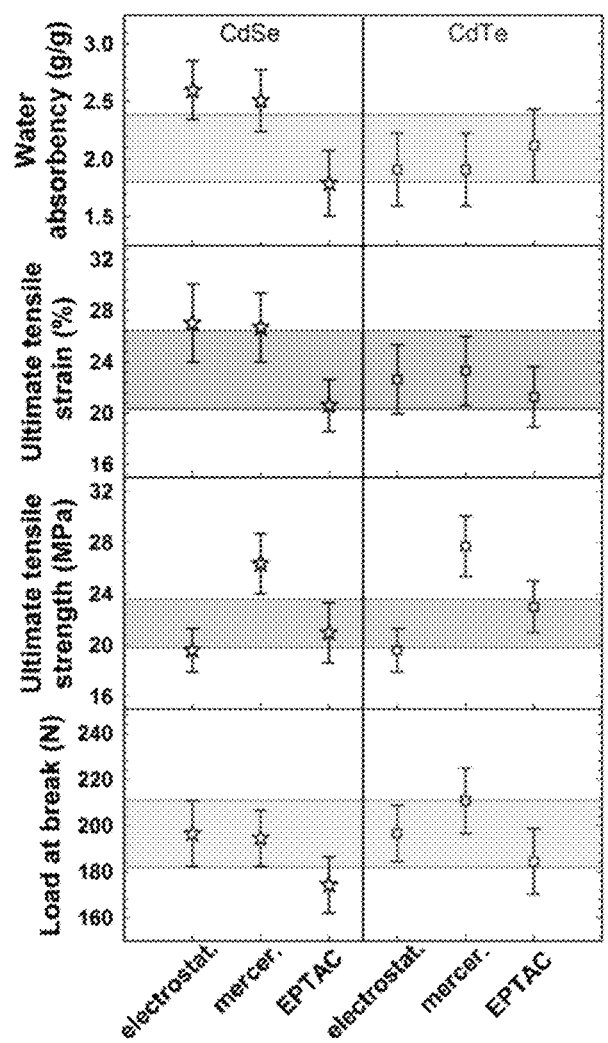
FIG. 3. Water absorbency and mechanical properties (ultimate tensile strain, ultimate tensile strength, and load at break) of cotton fibers functionalized with CdSe (open stars) and CdTe (open squares) NWs. Displayed are NW-functionalized textiles obtained using VDGG stimulated dip-coating (electrostat.), dip-coating onto mercerized cotton (mercer.), and dip-coating onto cationized cotton (EPTAC). For comparison purposes, bare cotton's typical range for each property is shown as a colored/shaded region.
Figure 20:
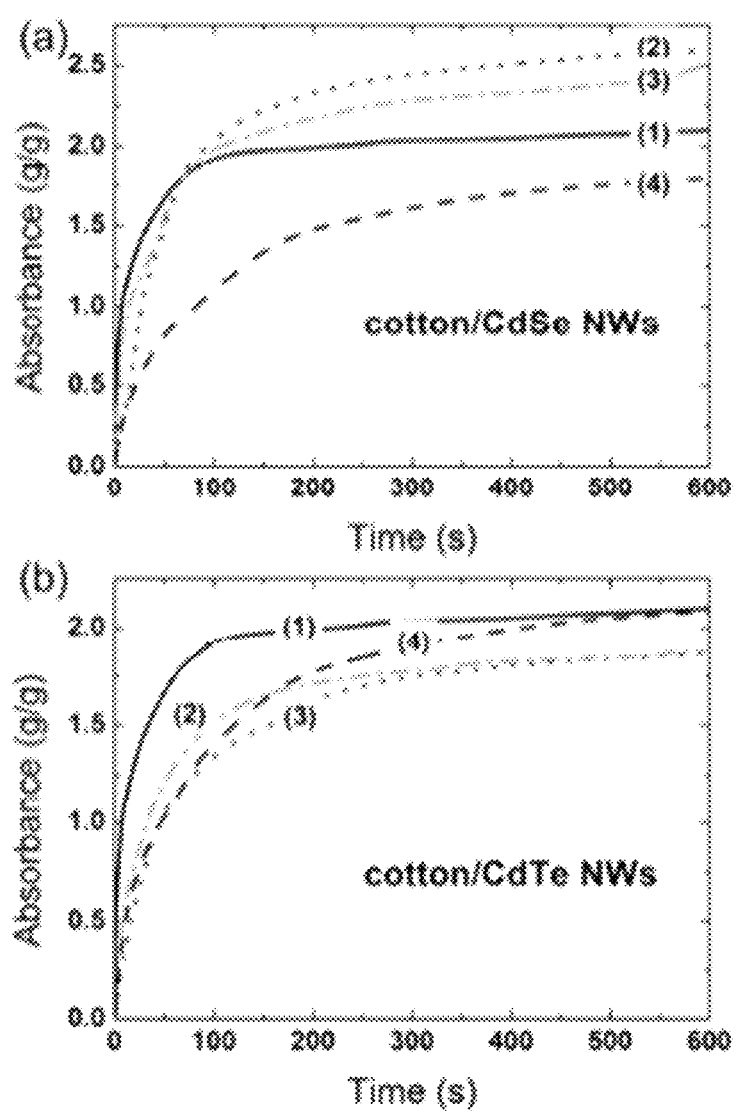
FIG. 20. Water absorbency as a function of time for (a) cotton/CdSe NW and (b) cotton/CdTe NW composites. In either case, bare cotton is trace (1), VDGG stimulated deposition is trace (2), NW deposition onto mercerized cotton is trace (3) and deposition onto cationized (EPTAC) cotton is trace (4).

FIG. 3 illustrates the water absorbency and mechanical properties (ultimate strain, ultimate strength and load at break) of unmodified cotton fabrics (colored/shaded regions) as well as those of cotton fabrics coated with CdSe (open stars) and CdTe (open squares) nanowires. Water uptake as a function of time can be found in FIG. 20. Neither the ability of cotton to absorb water nor the stiffness and extensibility of the fabrics is significantly compromised by the presence of NWs. In addition, durability tests designed to simulate normal garment washing procedures show that cotton/NW composites do not decompose, even after long (i.e., one week) washing periods (see FIG. 11).

Figure 4:
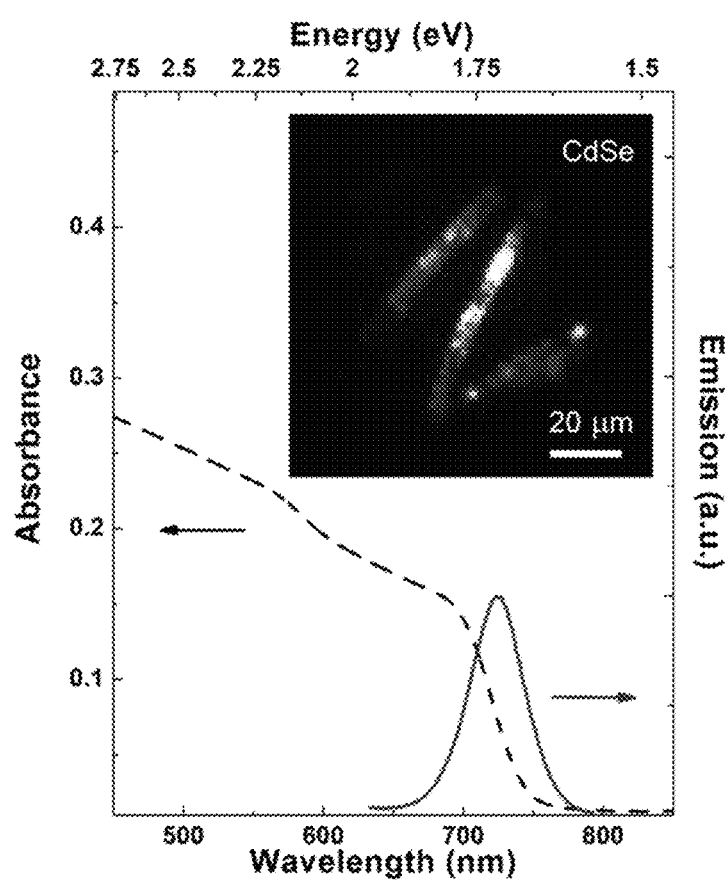
FIG. 4. Emission (solid line) and absorption (dashed line) spectra of the cotton/CdSe NW composite along with an emission image (false color) of individual CdSe NW-functionalized cotton fibers (inset).

At the same time, NW-functionalized cotton retains the native optical properties of the deposited wires. Specifically, in addition to the absorption spectra seen previously (FIG. 2 and FIG. 17), cotton/NW composites exhibit photoluminescence from the wires. FIG. 4 shows the corresponding band edge emission of cotton/CdSe NW composites. The inset is a false color emission image of individual cotton/CdSe NW fibers acquired with a microphotoluminescence setup. No photoluminescence is observed from CdTe samples as emission quantum yields of CdTe NWs are known to be lower than our instrument's detection limit Exemplary Applications.

Two possible applications using NW-functionalized cotton are barcoding and photodetectors. The first entails applying the unique Raman spectra of dielectric NWs to barcode cotton textiles. The second involves taking advantage of NW optical and electrical properties to make cotton-based photodetectors.

Using NW Raman Spectra to Barcode Cotton.

Figure 2:
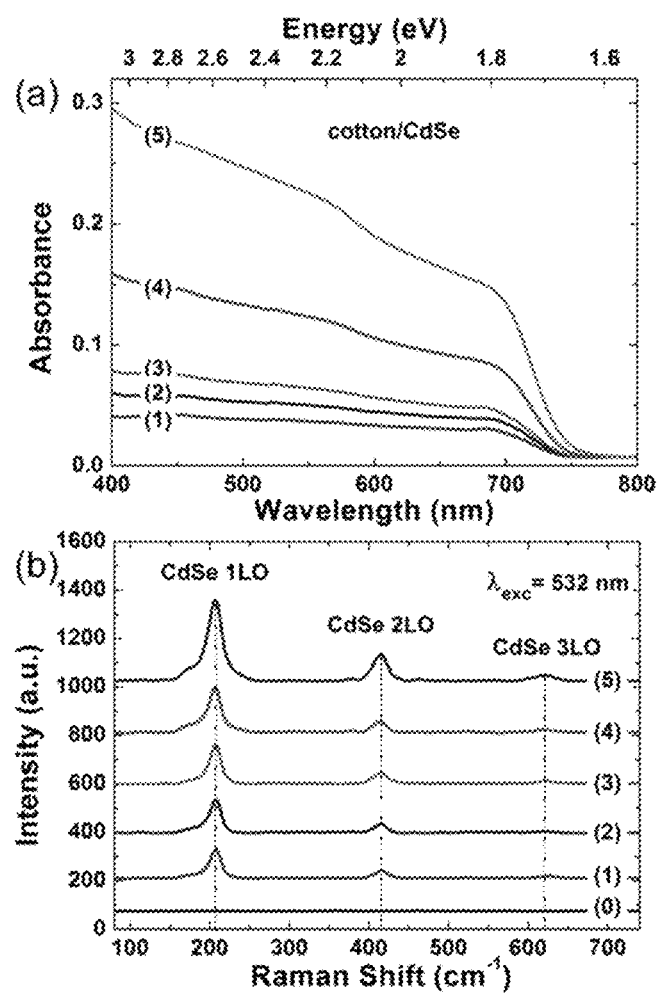
FIG. 2. (a) Absorbance spectra of cotton/CdSe NW textiles made with different deposition methods. From bottom to top, the labeled traces are: (1) simple dip-coating deposition of NWs, (2) light-induced dip-coating of NWs, (3) VDGG stimulated dip-coating deposition of NWs, (4) dip-coating deposition of NWs onto mercerized cotton, and (5) dip-coating deposition of NWs onto cationized cotton. (b) Raman spectra of the cotton/CdSe textiles, where numbered labels correspond to the same deposition approaches as in (a). For comparison purposes, the Raman spectrum for bare cotton is shown as trace (0). Traces offset for clarity.
Figure 5:
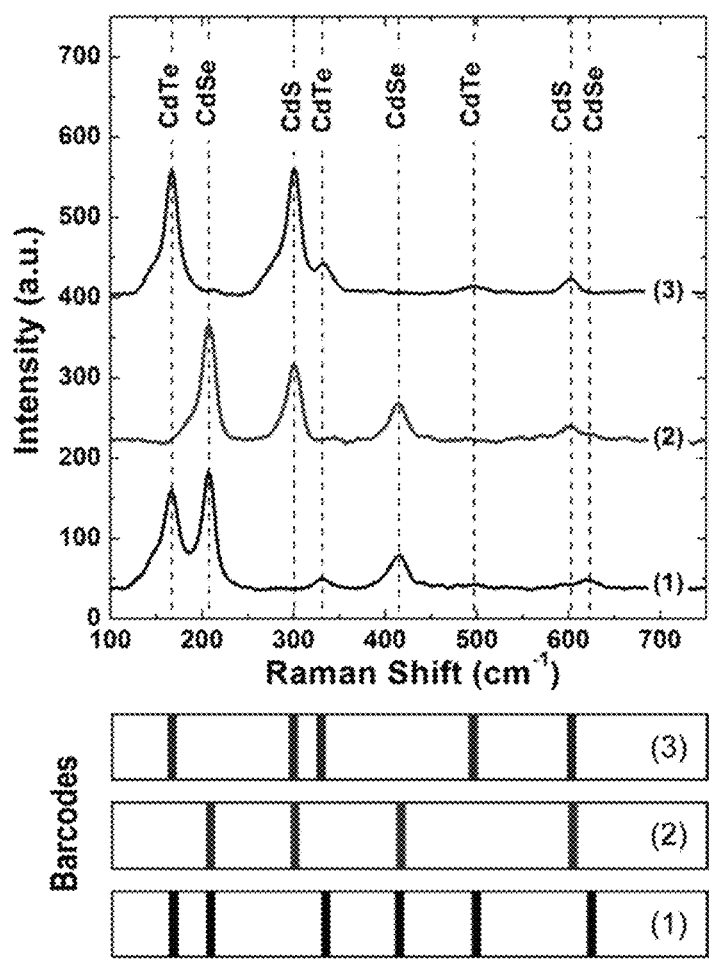
FIG. 5 Raman spectra of homogeneously mixed NW-EPTAC functionalized cotton fibers. From bottom to top: (1) cotton/CdSe/CdTe NW, (2) cotton/CdSe/CdS NW, (3) cotton/CdTe/CdS NW. Characteristic Raman lines for CdS, CdSe, and CdTe are shown for comparison purposes. Traces are offset for clarity. Barcodes obtained for each trace are shown below the plot.

NW-functionalized cotton textiles readily show Raman spectra characteristic of the deposited wires (FIG. 2). By functionalizing EPTAC cotton with a mixture of NW types, cotton textiles can be barcoded and used for identification purposes. This is illustrated in FIG. 5 where the Raman spectra of three cotton/mixed-NW composites are shown, specifically, cotton functionalized with a homogeneous mixture (50%/50%) of (1) CdSe+CdTe NWs, (2) CdSe+CdS NWs, and (3) CdS+CdTe NWs Raman spectra of all three composites show characteristic peaks for both NW species in each mixture. To illustrate, in the case of cotton/CdSe/CdS NW textiles [trace (2)], a set of CdSe peaks at $v_{1LO}$=205 cm$^{-1}$ and $v_{2LO}$=410 cm$^{-1}$ can be seen. Characteristic CdS peaks are also observed at $v_{1LO}$=300 cm$^{-1}$ and $v_{2LO}$=600 cm$^{-1}$. Analogous responses are seen with cotton/CdSe/CdTe [trace (1)] and cotton/CdTe/CdS textiles (trace 3). For comparison purposes, typical Raman lines of CdS, CdSe, and CdTe are shown as vertical dashed lines. Barcodes obtained for each trace are shown below the plot. More complex barcodes can be constructed by incorporating additional materials, such as ZnSe NWs (see FIG. 10). These experiments thus indicate potential uses of cotton/NW functionalization to create fiber-, yarn-, and fabric-based anti-counterfeiting systems that protect high-value textile products. Such fabrics could even be applied toward establishing positive identification mechanisms for the military, the police, and first responders.

Figure 6:
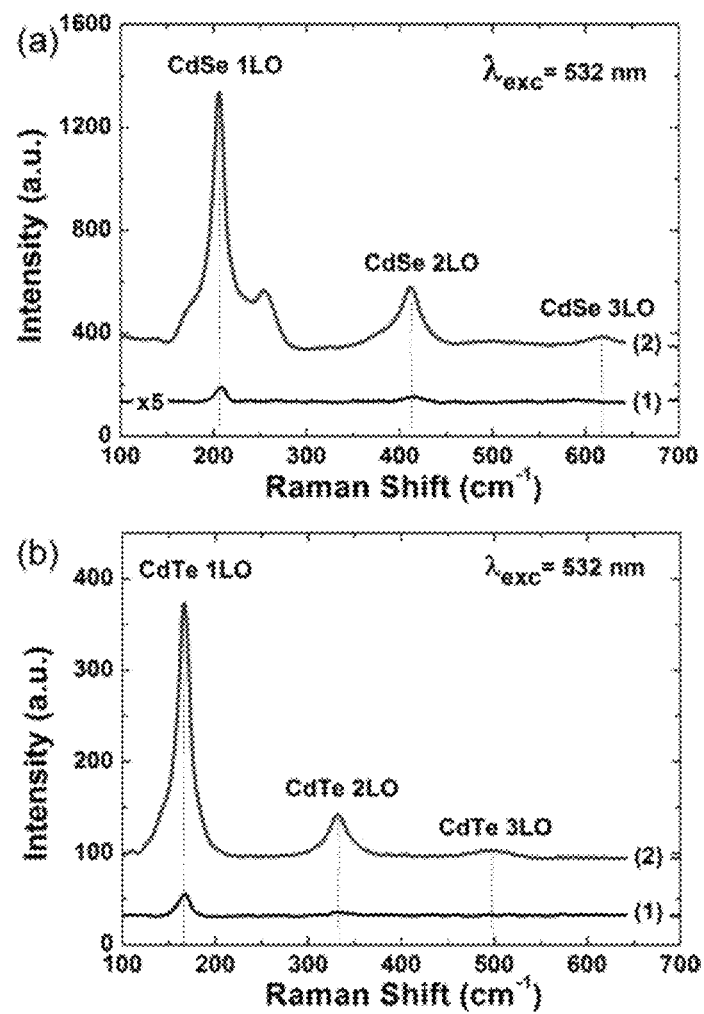
FIG. 6. (1) Regular and (2) surface-enhanced Raman spectra of (a) cotton/CdSe NW and (b) cotton/CdTe NW textiles made using dilute NW solutions. Traces are offset for clarity.
Figure 21:
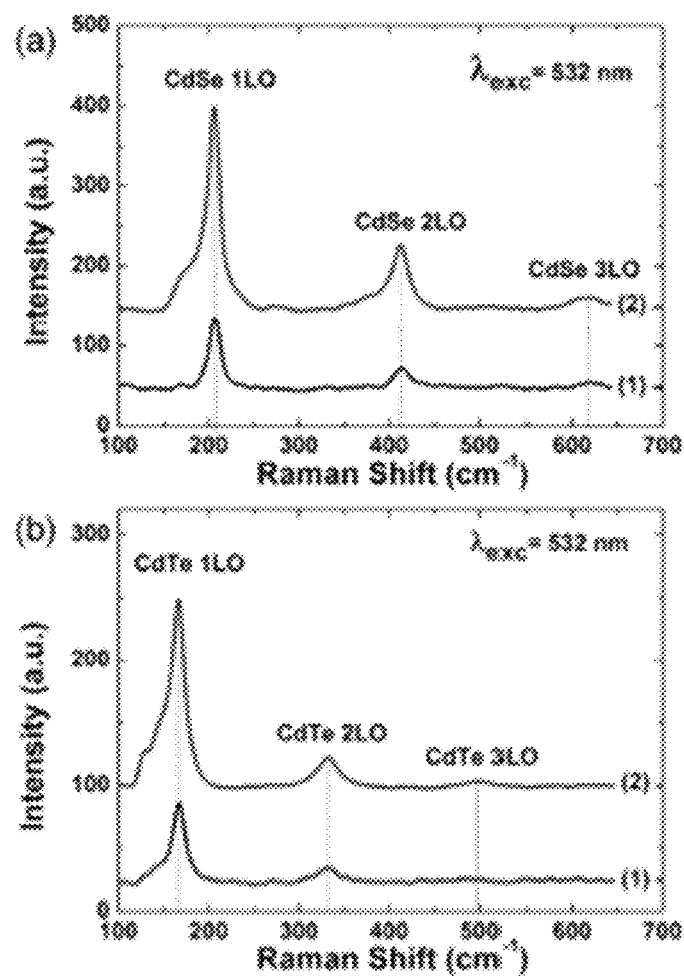
FIG. 21. Regular (1) and surface enhanced (2) Raman spectra of (a) cotton/CdSe NW and (b) cotton/CdTe NW textiles made using concentrated NW solutions. Traces are offset for clarity.
Figure 22:
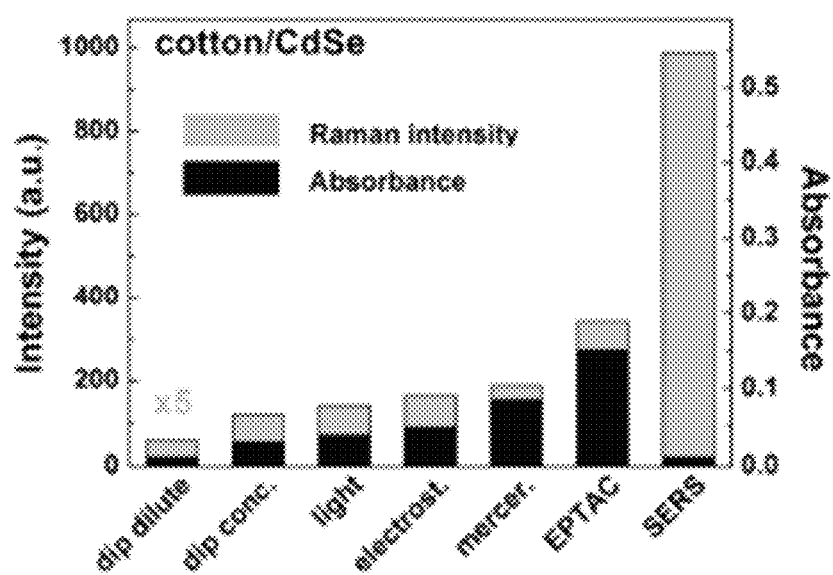
FIG. 22. Correlation of absorbance values (at 690 nm) and Raman intensities (at ~206 cm$^{-1}$) for CdSe NW-functionalized fabrics made using different deposition methods.
Figure 23:
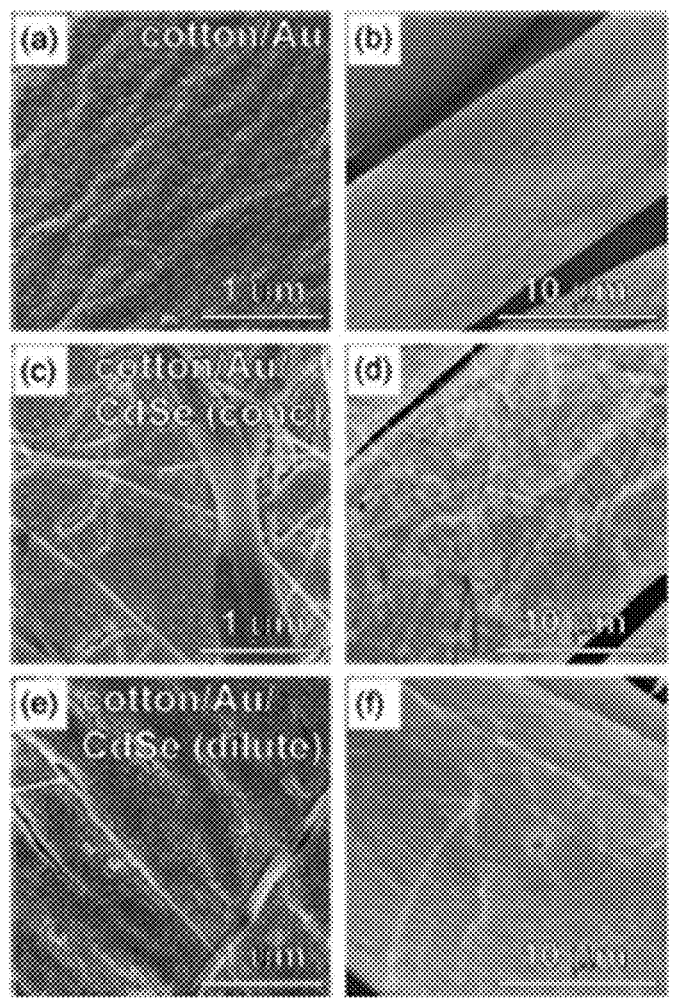
FIG. 23. SEM images of (a-b) locally purchased cotton/Au and (c-f) cotton/Au/CdSe NW composites. NWs were deposited onto the cotton by dip-coating the Au-functionalized cotton fabric with concentrated (c-d) and dilute (e-f) NW solutions.
Figure 24:
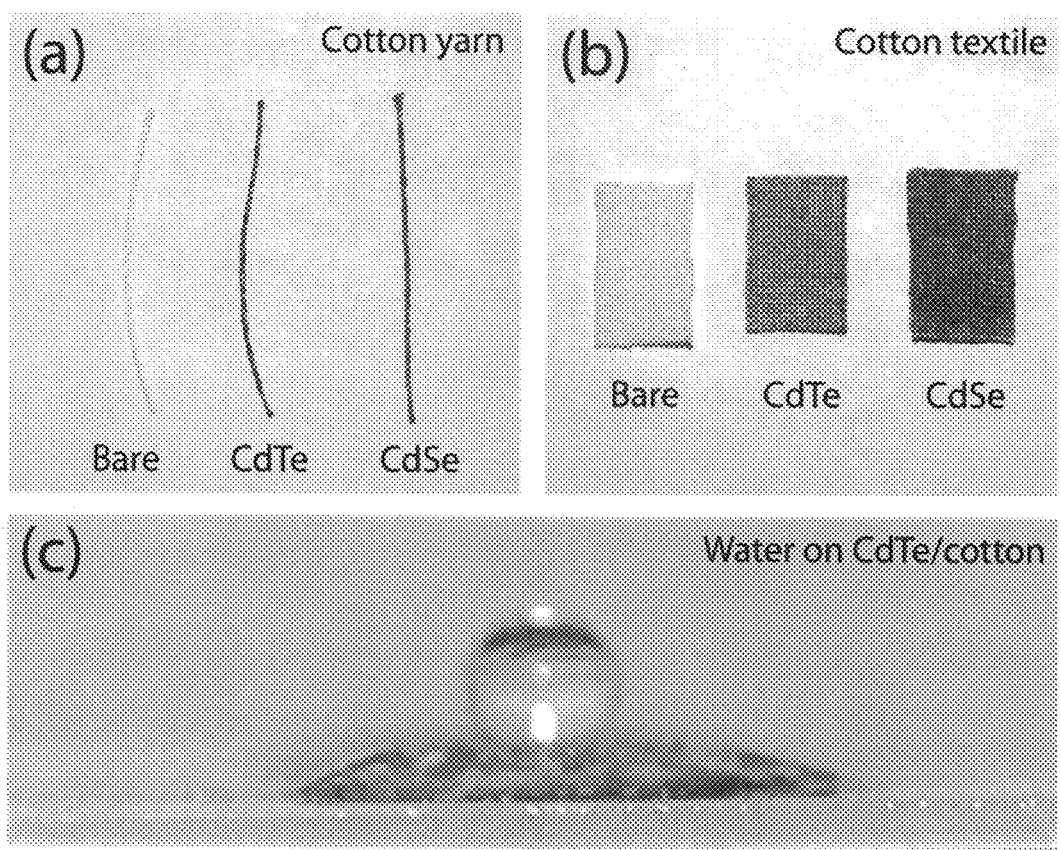
FIG. 24. Photographs of bare cotton yarn and textiles along with CdSe and CdTe nanowire coated counterparts (a, b) and resulting hydrophobicity (c).
Figure 25:
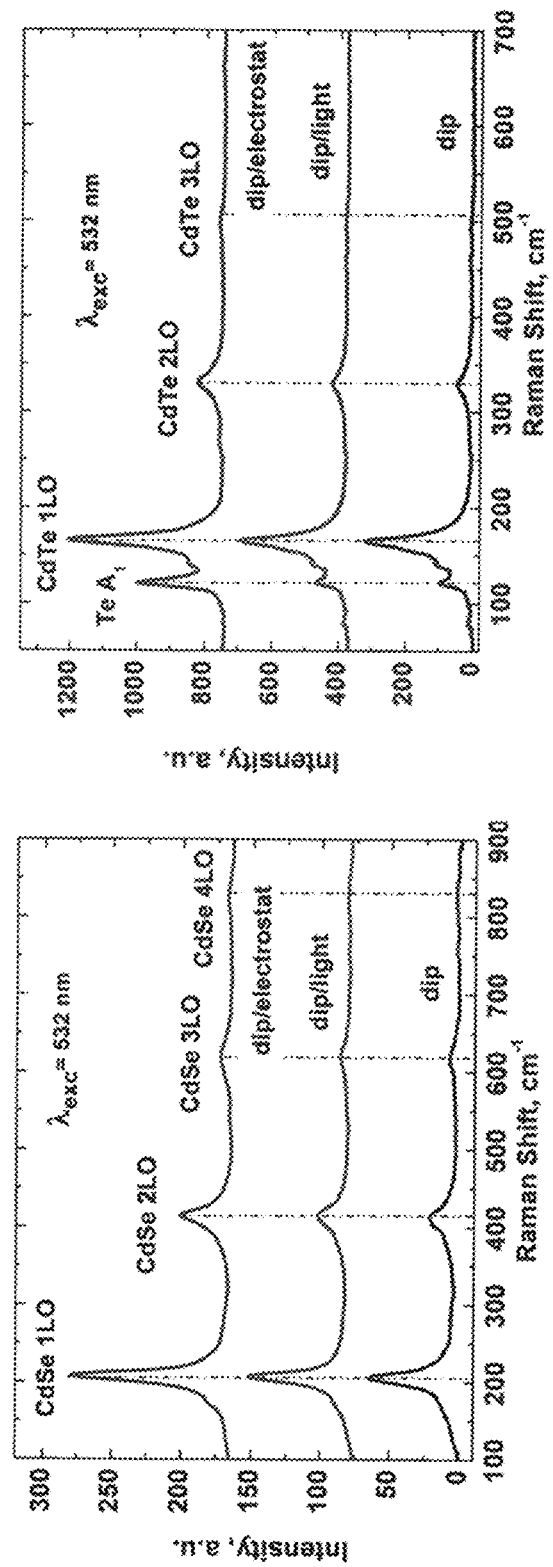
FIG. 25. Raman spectra of CdSe and CdTe functionalized cotton where the nanowires have been deposited in different manners as indicated on the graph.

Next, within the context of barcoding cotton, surface-enhancements mean that strong Raman signals can be obtained using less NWs, leading to cost-savings in manufacturing. Furthermore, enhanced signals are easier to detect at large distances, allowing for more flexible positive identification mechanisms. Accordingly, a thin film of Au (~100 nm) was sputtered onto cotton textiles. CdSe and CdTe NWs were then deposited onto these Au-coated cotton fibers through dip-coating. FIG. 6 shows resulting Raman spectra of cotton/CdSe NW/Au and cotton/CdTe NW/Au textiles. In either case, CdSe and CdTe LO phonon progressions (first seen in FIG. 2 and FIG. 18) are apparent. However, the primary difference from the earlier data is that the Raman intensities in FIG. 6 are approximately 25 times larger using 8 times less material (see FIG. 21). This highlights the use of surface enhancements as a cost saving measure, since larger Raman signals are produced using less material (see FIG. 22). SEM images of these cotton/NW/Au composites are provided in FIG. 23. The data in FIG. 6 therefore illustrate not only how cotton textiles cofunctionalized with NWs and Au can be used for barcoding purposes, but more generally, how functionalized cotton acquires the unique optical properties of its adsorbates.

Cotton-Based Photodetector.

Figure 7:
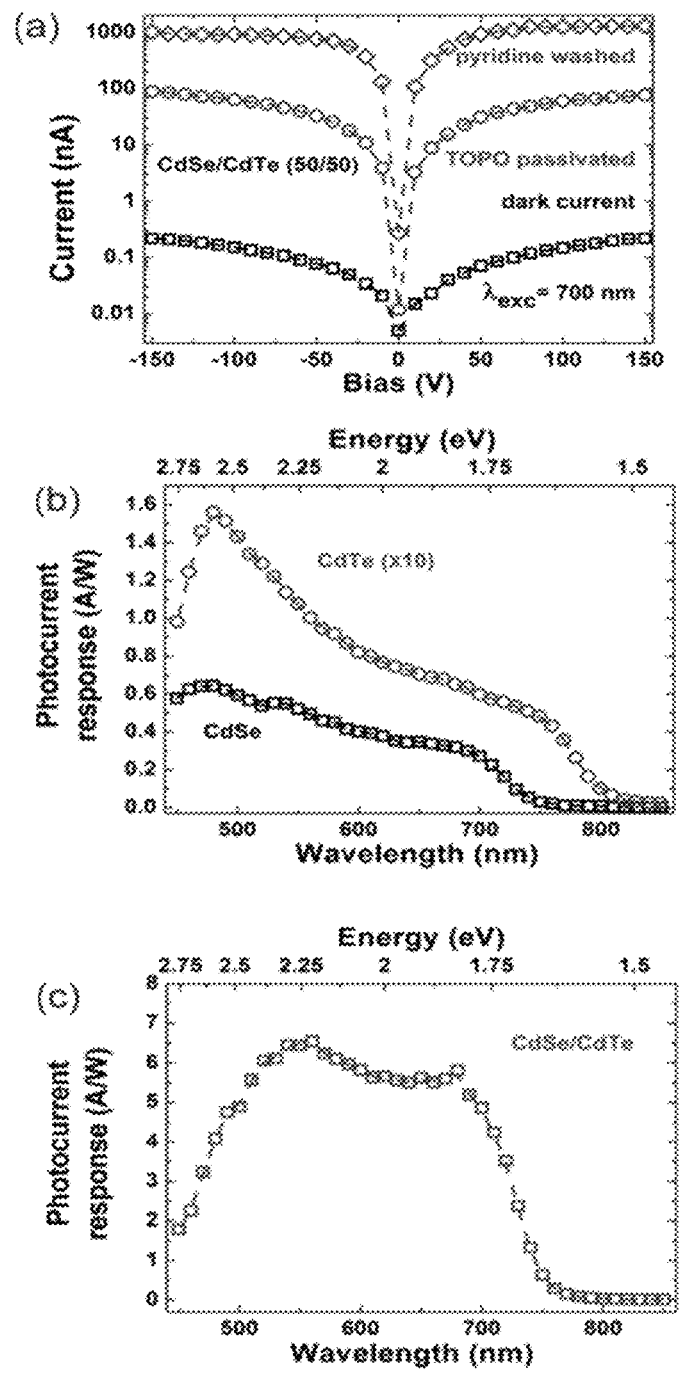
FIG. 7. (a) I-V characteristics and (b, c) photocurrent action spectra of locally purchased cotton functionalized with: (b) CdSe (open squares) and CdTe (open circles); and (c) homogeneously mixed (50%/50%) CdSe/CdTe NWs. Spectra in (b) and (c) were obtained with a +150 V bias.

In our second exemplary application, NW-functionalized cotton yarns were used to demonstrate a cotton-based photodetector. This takes advantage of the photoconductive nature of CdSe NWs. Cotton/NW yarns were placed between two gold electrodes with a 60 μm gap. A 150 V bias was applied across the electrodes and photocurrents were measured under illumination (additional details can be found herein). Under exposure to 700 nm light (297.6 mW/cm$^2$), the conductivities of cotton/NW yarns increase by more than 2 orders of magnitude (from 2×10$^{-5}$ to 6.8×10$^{-3}$ S m$^{-1}$). After pyridine treatment (described herein), cotton/NW yarn conductivities increase by an additional order of magnitude (to 1.2×10$^{-1}$ S m$^{-1}$). This is illustrated in FIG. 7a. The pyridine treatment enhances the composite's conductivity by removing excess TOPO from NW surfaces. TOPO is known to be an insulating species, which suppresses charge transport in close packed nanostructure films.

To ensure that measured photocurrents arise from the deposited NWs, photocurrent action spectra of cotton/NW composites was acquired by scanning the excitation wavelength during measurements. This is illustrated in FIG. 7b. The close resemblance of resulting photocurrent action spectra to the absorption of CdSe and CdTe NWs indicates that the wires are responsible for the observed photocurrent. Analogous results have been obtained for cotton/CdSe/CdTe NW yarns, consisting of homogeneously mixed CdSe and CdTe NWs (FIG. 7c).

Figure 26:
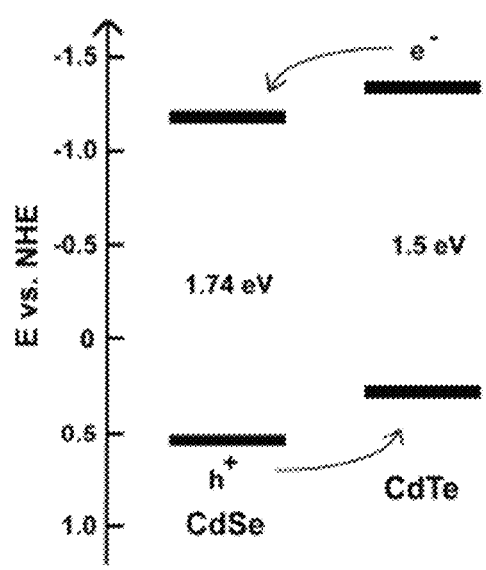
FIG. 26. Energy Level Diagram of CdSe/CdTe composites. Band positions of bulk CdSe and CdTe are used.
Figure 27:
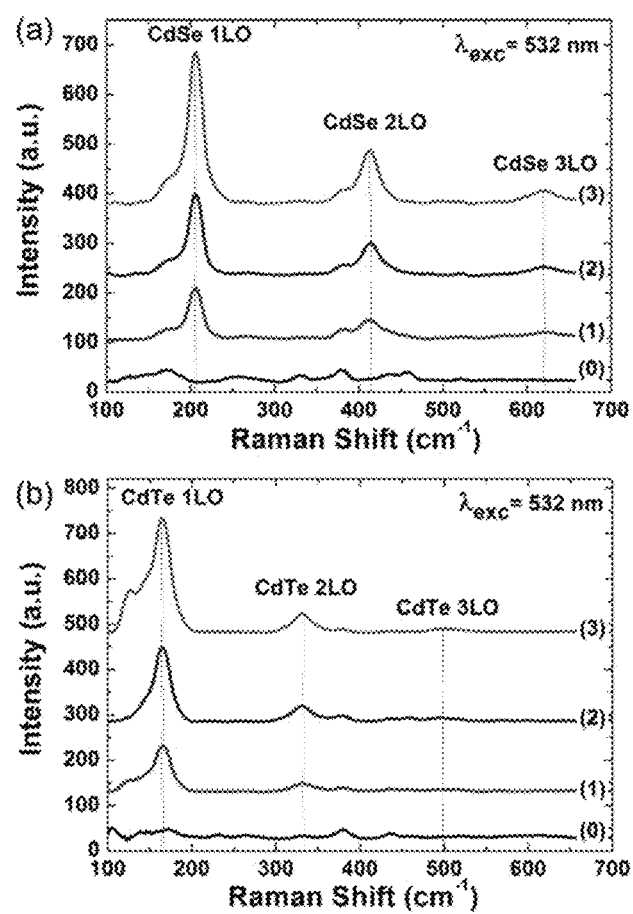
FIG. 27. Raman spectra of other CdSe and CdTe functionalized cotton.
Figure 28:
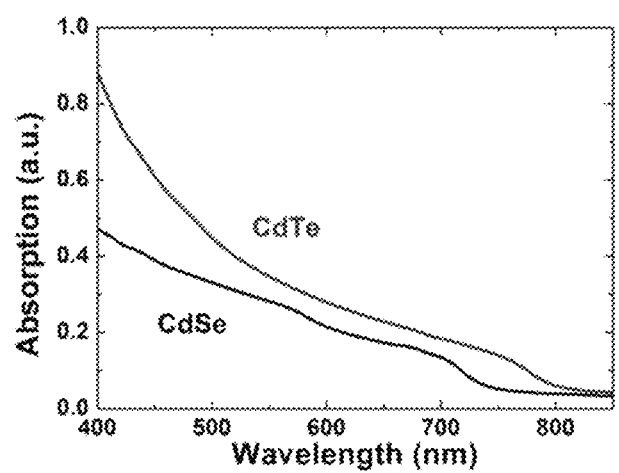
FIG. 28. Linear absorption spectra of other CdSe and CdTe NW solutions.

Homogeneously mixed (CdSe/CdTe) NW composites exhibit improved photoconductivities over comparable cotton/CdSe NW and cotton/CdTe NW devices. This may be attributed to the enhanced charge separation efficiencies that exist in CdSe/CdTe mixtures, stemming from their mutual Type-II band offsets. As a consequence, photogenerated electrons in CdTe migrate into CdSe's conduction band while photogenerated holes in CdSe migrate to CdTe's valence band (see FIG. 26). This prevents unwanted electron-hole recombination and better enables the external field to extract both types of charges. The photocurrent response of cotton/CdSe/CdTe NW devices begins around the band edge of CdSe (FIG. 7c). This likely implies that photogenerated carriers in CdTe are highly susceptible to trapping into defect states.

Functionalization of cotton textiles with solution-based dielectric NWs using various physical and chemical approaches was demonstrated. What results are uniform and conformal coatings, wherein individual cotton fibers are encapsulated by an interlinked NW network. As produced textiles retain cotton's inherent mechanical and absorptive qualities, but are imparted with the unique optical and electrical properties of the NWs. The demonstrated functionalization of cotton is general and NW coatings using other compositions are possible given the solution processability of these wires. Furthermore, two proof-of-concept applications have been demonstrated to illustrate potential uses for these composites. The first entails barcoding cotton using the unique Raman signature of the NWs. A surface-enhancement effect is also demonstrated when Au is co-deposited onto cotton, allowing for enhanced Raman signals using significantly lower NW concentrations. The second proof-of-concept application illustrates a cotton-based photodetector which utilizes the intrinsic photoconductivity of CdSe NWs. Beyond these two examples, NW-functionalized cotton may possess other potential uses in areas ranging from anti-counterfeiting to positive identification devices.

Example 2

The following provides examples of the nanowire-functionalized fibers of the present disclosure and methods of making the functionalized fibers.

ZnSe Nanowire Synthesis:

ZnSe NWs were prepared following a described method with some modifications. To make ZnSe NWs, TOPO (2.5 g, 6.5 mmol) and zinc stearate (30 mg, 47.5 μmol) were combined in a three neck flask connected to a Schlenk line.

The mixture was stirred under vacuum at 150° C. for 1 hour to dry and degas it. The reaction vessel was back-filled with $N_2$ and was heated to 310° C. An injection solution, consisting of 1 M TOPSe (25.0 μL, 25.0 μmol) and 2 mM BiCl3 in acetone (50.0 μL, 0.1 μmol), was then rapidly introduced into the three-neck flask. A yellow solution resulted due to the formation of NWs. The solution was subsequently left at 310° C. for 30 minutes and was cooled to 75° C. to stop the reaction. Toluene (15.0 mL) was added to prevent TOPO from solidifying. Produced NWs were precipitated from suspension by adding an excess of methanol (10.0 mL). The wires were recovered by centrifuging this mixture and were subsequently subjected to several toluene/methanol washing steps to remove any excess TOPO. Resulting NWs were stored in toluene.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

The invention claimed is:

1. A method for making an organic or inorganic fiber having disposed on at least a portion of its surface one or more nanowires having a cross-sectional diameter of 1 to 75 nm and a length of 1 to 10 microns or a composition comprising a plurality of the organic or inorganic fibers comprising:
    a) contacting a precursor fiber or plurality of precursor fibers with a suspension comprising nanowires in a solvent and irradiating the suspension with broadband visible light while the precursor fiber or precursor fibers is/are dipped into the suspension;
    b) removing the precursor fiber or precursor fibers from the suspension, wherein one or more nanowires are disposed on at least a portion of a surface of the precursor fiber or precursor fibers; and
    c) drying the fiber or fibers from b) to provide the organic or inorganic fiber or the composition comprising a plurality of the organic or inorganic fibers.

2. The method of claim 1, wherein the precursor fiber comprises cationic cellulose, anionic cellulose, ester-modified cellulose, or mercerized cotton.

3. The method of claim 1, wherein the broadband visible light has a power density of at least 100 mW/cm² and/or a wavelength of 300 to 2000 nm.

4. The method of claim 1, further comprising electrostatically charging the precursor fiber or precursor fibers to form a charged fiber prior to the dipping.

5. The method of claim 1, wherein the fiber is an organic fiber, and wherein the organic fiber is a cellulose fiber, polyacrylonitrile (PAN) fiber, or a polyamide fiber.

6. The method of claim 1, wherein the fiber is an inorganic fiber, and wherein the inorganic fiber is a zirconia fiber.

7. The method of claim 1, wherein the nanowires are comprised of CdSe, CdTe, CdS, ZnO, ZnS, ZnSe, ZnTe, PbS, PbSe, PbTe, $PbSe_xS_{1-x}$, wherein x is 0 to 1, InN, InP, InAs, GaP, GaN, GaAs, $TiO_2$, or combinations thereof.

8. The method of claim 1, wherein the fiber has one or more metal nanoparticles disposed on at least a portion of a fiber surface and/or at least a portion of a nanowire surface.

9. The method of claim 1, wherein the nanowire is bound to the fiber via electrostatic forces, van der Waal forces, covalent bonds, or a combination thereof.

10. The method of claim 1, wherein the composition is a plurality of the woven fibers.

11. The method of claim 1, wherein the organic or inorganic fiber does not have a nanoparticle disposed on a surface of the organic or inorganic fiber.

12. A method for determining the presence or absence of an organic or inorganic fiber having disposed on at least a portion of its surface one or more nanowires having a cross-sectional diameter of 1 to 75 nm and a length of 1 to 10 microns or a composition comprising a plurality of the organic or inorganic fibers in a sample comprising:
    a) obtaining a test infrared, Raman, and/or x-ray fluorescence spectrum of the sample;
    b) comparing the test infrared, Raman, and/or x-ray fluorescence spectrum to at least one control infrared, Raman, and/or x-ray fluorescence spectrum, wherein the control infrared, Raman, and/or x-ray fluorescence spectrum is an infrared, Raman, or x-ray fluorescence spectrum of a control fiber or a control composition; and
    c) determining a presence of selected features of the control infrared, Raman, and/or x-ray fluorescence spectrum in the test infrared, Raman, and/or x-ray fluorescence spectrum, wherein the presence of the selected features of the control infrared, Raman, and/or x-ray fluorescence spectrum in the test infrared, Raman, and/or x-ray fluorescence spectrum is indicative of the presence of the organic or inorganic fiber or the composition comprising a plurality of the organic or inorganic fibers in the sample and a lack of the selected features of the control infrared, Raman, and/or x-ray fluorescence spectrum in the test infrared, Raman, and/or x-ray fluorescence spectrum is indicative of the absence of the organic or inorganic fiber or the composition comprising a plurality of the organic or inorganic fibers in the sample.

13. The method of claim 12, wherein the sample is paper currency comprising cellulose.

14. The method of claim 12, wherein the fiber is an organic fiber, and wherein the organic fiber is a cellulose fiber, polyacrylonitrile (PAN) fiber, or a polyamide fiber.

15. The method of claim 12, wherein the fiber is an inorganic fiber, and wherein the inorganic fiber is a zirconia fiber.

16. The method of claim 12, wherein the nanowires are comprised of CdSe, CdTe, CdS, ZnO, ZnS, ZnSe, ZnTe, PbS, PbSe, PbTe, $PbSe_xS_{1-x}$, wherein x is 0 to 1, InN, InP, InAs, GaP, GaN, GaAs, $TiO_2$, or combinations thereof.

17. The method of claim 12, wherein the fiber has one or more metal nanoparticles disposed on at least a portion of a fiber surface and/or at least a portion of a nanowire surface.

18. The method of claim 12, wherein the nanowire is bound to the fiber via electrostatic forces, van der Waal forces, covalent bonds, or a combination thereof.

19. The method of claim 12, wherein the composition is a plurality of the woven fibers.

20. The method of claim 12, wherein the organic or inorganic fiber does not have a nanoparticle disposed on a surface of the organic or inorganic fiber.

21. A method for determining presence or absence of electromagnetic radiation having a wavelength of 300 to 3000 nm comprising:
    a) providing an organic or inorganic fiber having disposed on at least a portion of its surface one or more nanowires having a cross-sectional diameter of 1 to 75 nm and a length of 1 to 10 microns or a composition comprising a plurality of the organic or inorganic fibers, wherein the fiber or fibers absorb electromagnetic radiation having a wavelength of 300 to 3000 nm; and b) determining magnitude of an electrical current, wherein generation of an electrical current is indicative of the presence of electromagnetic radiation having a wavelength of 300 to 3000 nm and absence of the generation of an electrical current is indicative of absence of electromagnetic radiation having a wavelength of 300 to 3000 nm.

22. The method of claim 21, wherein the intensity of the electromagnetic radiation present is based on a magnitude of the electrical current.

* * * * *